(12) United States Patent
Dong et al.

(10) Patent No.: US 7,521,527 B2
(45) Date of Patent: Apr. 21, 2009

(54) GLP-1 PHARMACEUTICAL COMPOSITIONS

(75) Inventors: Zheng Xin Dong, Holliston, MA (US);
Roland Cherif-Cheikh, Barcelona (ES)

(73) Assignee: Societe de Conseils de Recherches et d'Applications Scientifiques, S.A.S., Paris (FR)

(*) Notice: Subject to any disclaimer, the term of this patent is extended or adjusted under 35 U.S.C. 154(b) by 208 days.

(21) Appl. No.: 11/015,615

(22) Filed: Dec. 16, 2004

(65) Prior Publication Data

US 2005/0159356 A1 Jul. 21, 2005

Related U.S. Application Data

(60) Provisional application No. 60/529,932, filed on Dec. 16, 2003.

(51) Int. Cl.
C07K 14/605 (2006.01)
A61K 38/26 (2006.01)

(52) U.S. Cl. ............................. 530/308; 514/2; 514/12; 530/300; 530/324

(58) Field of Classification Search .................. 514/2, 514/12; 530/308, 300, 324
See application file for complete search history.

(56) References Cited

U.S. PATENT DOCUMENTS

| | | | |
|---|---|---|---|
| 4,783,441 A * | 11/1988 | Thurow ........................... | 514/3 |
| 5,512,549 A | 4/1996 | Chen et al. | |
| 5,545,618 A | 8/1996 | Buckley et al. | |
| 5,595,760 A | 1/1997 | Cherif-Cheikh | |
| 5,705,483 A | 1/1998 | Galloway et al. | |
| 5,977,071 A | 11/1999 | Galloway et al. | |
| 5,980,945 A | 11/1999 | Ruiz | |
| 6,221,958 B1 | 4/2001 | Shalaby et al. | |
| 6,284,727 B1 * | 9/2001 | Kim et al. ...................... | 514/12 |
| 6,380,357 B2 | 4/2002 | Hermeling et al. | |
| 6,410,513 B1 | 6/2002 | Galloway et al. | |
| 6,458,924 B2 | 10/2002 | Knudsen et al. | |
| 6,482,864 B1 | 11/2002 | Yamagata et al. | |
| 6,503,534 B1 | 1/2003 | Pellet et al. | |
| 6,555,521 B2 * | 4/2003 | Hermeling et al. ............ | 514/12 |
| 6,566,490 B1 | 5/2003 | Manique et al. | |
| 6,620,910 B1 | 9/2003 | Calas et al. | |
| 6,663,899 B2 | 12/2003 | Cleland et al. | |
| 6,696,500 B2 | 2/2004 | Hata et al. | |
| 6,703,365 B2 * | 3/2004 | Galloway et al. ............. | 514/12 |
| 6,720,407 B1 | 4/2004 | Hughes et al. | |
| 6,903,186 B1 | 6/2005 | Dong et al. | |
| 7,084,243 B2 * | 8/2006 | Glaesner et al. ............. | 530/300 |
| 2001/0006943 A1 | 7/2001 | Jensen et al. | |
| 2002/0165342 A1 | 11/2002 | Galloway et al. | |
| 2003/0045464 A1 | 3/2003 | Hermeling et al. | |
| 2003/0050237 A1 | 3/2003 | Kim et al. | |
| 2003/0186858 A1 | 10/2003 | Arentsen | |
| 2003/0195157 A1 | 10/2003 | Natarajan et al. | |
| 2003/0220243 A1 | 11/2003 | Glaesner et al. | |

FOREIGN PATENT DOCUMENTS

| | | |
|---|---|---|
| EP | 0 619 322 | 10/1994 |
| EP | 0 658 568 | 6/1995 |
| EP | 0 699 686 | 3/1996 |
| EP | 0 708 179 | 4/1996 |
| EP | 0 733 644 | 9/1996 |
| EP | 0 869 135 | 10/1998 |
| EP | 1 061 946 | 4/2004 |
| FR | 2 777 283 | 10/1999 |
| WO | 87/06941 | 11/1987 |
| WO | 91/11457 | 8/1991 |
| WO | 97/29180 | 8/1997 |
| WO | 98/03457 | 1/1998 |
| WO | 98/08871 | 3/1998 |
| WO | 98/19698 | 5/1998 |
| WO | 99/30731 | 6/1999 |
| WO | 99/43705 | 9/1999 |
| WO | 00/34331 | 6/2000 |
| WO | 01/00223 | 1/2001 |
| WO | 01/157084 | 8/2001 |
| WO | 03/035099 | 5/2003 |

OTHER PUBLICATIONS

Kim et al., "The application of crystal soaking technique to study the effect of zinc and cresol on insulinotropin crystals grown from a saline solution," Pharma. Res., 1995, 12(11):1664-1670.

Pridal et al., "Absorption of glucagons-like peptide-1 can be protracted by zinc or protamine," Int. J. Pharmaceutics, 1996, 136:53-59.

Deacon, C.F., et al.; "Dipeptidyl peptidase IV resistant analogues of glucagon-like peptide-1 which have extended metabolic stability and improved biological activity"; 1998; Diabetologia; vol. 41; pp. 271-278.

Parker, J. et al., "Structure-function analysis of a series of glucagons-like peptide-1 analogs," J. Peptide Res., 1998, 52:398-409.

Abstract of Hungarian Patent P9501508 published Feb. 28, 1997 (Hungarian and English languages).

Choi, S. et al., "Control of blood glucose by novel GLP-1 deliver using biodegradable triblock copolymer of PLGA-PEG-PLGA in type 2 diabetic rats," Pharm. Res. 21(5):827-831, 2004.

Fowers, K. D. et al., "Thermally reversible gelling materials for safe and versatile depot delivery," Drug Delivery Technology, 3(5) Jul./Aug. 2003.

* cited by examiner

*Primary Examiner*—David Lukton
(74) *Attorney, Agent, or Firm*—Yankwich & Associates, P.C.; Leon R. Yankwich; Michael R. Wesolowski

(57) ABSTRACT

The present invention is directed to peptide analogues of glucagon-like peptide-1, the pharmaceutically-acceptable salts thereof, to methods of using such analogues to treat mammals and to pharmaceutical compositions useful therefor comprising said analogues.

9 Claims, 4 Drawing Sheets

GLP-1 PHARMACEUTICAL COMPOSITIONS

This application claims benefit of U.S. Provisional patent application No. 60/529,932, filed Dec. 16, 2003.

BACKGROUND OF THE INVENTION

The present invention is directed to peptide analogues of glucagon-like peptide-1, the pharmaceutically-acceptable salts thereof, to methods of using such analogues to treat mammals and to pharmaceutical compositions useful therefor comprising said analogues.

Glucagon-like peptide-1 (7-36) amide (GLP-1) is synthesized in the intestinal L-cells by tissue-specific post-translational processing of the glucagon precursor preproglucagon (Varndell, J. M., et al., J. Histochem Cytochem, 1985:33: 1080-6) and is released into the circulation in response to a meal. The plasma concentration of GLP-1 rises from a fasting level of approximately 15 pmol/L to a peak postprandial level of 40 pmol/L. It has been demonstrated that, for a given rise in plasma glucose concentration, the increase in plasma insulin is approximately threefold greater when glucose is administered orally compared with intravenously (Kreymann, B., et al., Lancet 1987:2, 1300-4). This alimentary enhancement of insulin release, known as the incretin effect, is primarily humoral and GLP-1 is now thought to be the most potent physiological incretin in humans. In addition to the insulinotropic effect, GLP-1 suppresses glucagon secretion, delays gastric emptying (Wettergren A., et al., Dig Dis Sci 1993:38: 665-73) and may enhance peripheral glucose disposal (D'Alessio, D. A. et al., J. Clin Invest 1994:93:2293-6).

In 1994, the therapeutic potential of GLP-1 was suggested following the observation that a single subcutaneous (s/c) dose of GLP-1 could completely normalize postprandial glucose levels in patients with non-insulin-dependent diabetes mellitus (NIDDM) (Gutniak, M. K., et al., Diabetes Care 1994:17:1039-44). This effect was thought to be mediated both by increased insulin release and by a reduction in glucagon secretion. Furthermore, an intravenous infusion of GLP-1 has been shown to delay postprandial gastric emptying in patients with NIDDM (Williams, B., et al., J. Clin Endo Metab 1996:81:327-32). Unlike sulphonylureas, the insulinotropic action of GLP-1 is dependent on plasma glucose concentration (Holz, G. G. $4^{th}$, et al., Nature 1993:361:362- 5). Thus, the loss of GLP-1-mediated insulin release at low plasma glucose concentration protects against severe hypoglycemia. This combination of actions gives GLP-1 unique potential therapeutic advantages over other agents currently used to treat NIDDM.

Numerous studies have shown that when given to healthy subjects, GLP-1 potently influences glycemic levels as well as insulin and glucagon concentrations (Orskov, C, Diabetologia 35:701-711, 1992; Holst, J. J., et al., *Potential of GLP-1 in diabetes management* in Glucagon III, Handbook of Experimental Pharmacology, Lefevbre P J, Ed. Berlin, Springer Verlag, 1996, p. 311-326), effects which are glucose dependent (Kreymann, B., et al., Lancet ii: 1300-1304, 1987; Weir, G. C., et al., Diabetes 38:338-342, 1989). Moreover, it is also effective in patients with diabetes (Gutniak, M., N. Engl J Med 226:1316-1322, 1992; Nathan, D. M., et al., Diabetes Care 15:270-276, 1992), normalizing blood glucose levels in type 2 diabetic subjects (Nauck, M. A., et al., Diagbetologia 36:741-744, 1993), and improving glycemic control in type 1 patients (Creutzfeldt, W. O., et al., Diabetes Care 19:580-586, 1996), raising the possibility of its use as a therapeutic agent.

GLP-1 is, however, metabolically unstable, having a plasma half-life ($t_{1/2}$) of only 1-2 min in vivo. Exogenously administered GLP-1 is also rapidly degraded (Deacon, C. F., et al., Diabetes 44:1126-1131, 1995). This metabolic instability limits the therapeutic potential of native GLP-1.

A number of attempts have been taken to improve the therapeutic potential of GLP-1 and its analogs through improvements in formulation. For example, International patent publication no. WO 01/57084 describes a process for producing crystals of GLP-1 analogues which are said to be useful in the preparation of pharmaceutical compositions, such as injectable drugs, comprising the crystals and a pharmaceutical acceptable carrier. Heterogeneous micro crystalline clusters of GLP-1(7-37)OH have been grown from saline solutions and examined after crystal soaking treatment with zinc and/or m-cresol (Kim and Haren, Pharma. Res. Vol. 12 No. 11 (1995)). Crude crystalline suspensions of GLP(7-36) $NH_2$ containing needle-like crystals and amorphous precipitation have been prepared from phosphate solutions containing zinc or protamine (Pridal, et. al., International Journal of Pharmaceutics Vol. 136, pp. 53-59 (1996)). European patent publication no. EP 0619322A2 describes the preparation of micro-crystalline forms of GLP-1 (7-37)OH by mixing solutions of the protein in pH 7-8.5 buffer with certain combinations of salts and low molecular weight polyethylene glycols (PEG). U.S. Pat. No. 6,566,490 describes seeding microcrystals of, inter alia, GLP-1 which are said to aid in the production of purified peptide products. U.S. Pat. No. 6,555,521 (US '521) discloses GLP-1 crystals having a tetragonal flat rod or a plate-like shape which are said to have improved purity and to exhibit extended in vivo activity. US '521 teaches that such crystals are relatively uniform and remain in suspension for a longer period of time than prior crystalline clusters and amorphous crystalline suspensions which were said to settle rapidly, aggregate or clump together, clog syringe needles and generally exacerbate unpredictable dosing.

A biodegradable triblock copolymer of poly [(dl-lactide-co-glycolide)-b-ethylene glycol-b-(-lactide-co-glycolide)] has been suggested for use in a controlled release formulation of GLP-1. However like other polymeric systems, the manufacture of triblock copolymer involves complex protocols and inconsistent particulate formation.

Similarly, biodegradable polymers, e.g., poly(lactic-co-glycolic acid) (PLGA), have also been suggested for use in sustained delivery formulations of peptides. However the use of such biodegradable polymers has been disfavored in the art since these polymers generally have poor solubility in water and require water-immiscible organic solvents, e.g., methylene chloride, and/or harsh preparation conditions during manufacture. Such organic solvents and/or harsh preparation conditions are considered to increase the risk of inducing conformational change of the peptide or protein of interest, resulting in decreased structural integrity and compromised biological activity. (Choi et al., Pharm. Research, Vol. 21, No. 5, (2004).) Poloxamers have been likewise faulted. (Id.)

The GLP-1 compositions described in the foregoing references are less than ideal for preparing pharmaceutical formulations of GLP's since they tend to trap impurities and/or are otherwise difficult to reproducibly manufacture and administer. Also, GLP analogs are known to induce nausea at elevated concentrations, thus there is a need to provide a sustained drug effect with reduced initial plasma concentrations. Hence, there is a need for GLP-1 formulations which are more easily and reliably manufactured, that are more easily and reproducibly administered to a patient, and that provide for reduced initial plasma concentrations in order to reduce or eliminate unwanted side-effects.

SUMMARY OF THE INVENTION

The invention may be summarized in the following paragraphs (1) through (67), below, as well as the claims. Accordingly:

(1) In one aspect the present invention is directed to a pharmaceutical composition comprising at least one insulinotropic molecule from glucagon-like peptide-1, exendin4, and analogs and derivatives thereof, whose aqueous solubility is lower than 1 mg/mL, preferably lower than 0.5 mg/mL, at pH between 6 and 8 and at about 4-40° C.

(2) Preferably said insulinotropic molecule has an isoelectric point about 5-9, more preferably about 6-8, provided that the molecule is not human GLP-1 (7-36)$NH_2$ or human GLP-1 (7-37)-OH.

(3) In one embodiment the invention features a composition according to paragraph (1), further comprising water.

(4) A composition according to any one of paragraphs (1) to (3), further comprising non-aqueous medium.

(5) A composition according to any one of paragraphs (1) to (4) wherein the molecule is present in an aqueous solution with pH lower than 7, preferably lower than 5.

(6) A composition according to any one of paragraphs (1) to (5), wherein the molecule is present in a clear solution with pH equal or lower than 4.5.

(7) A composition according to any one of paragraphs (1) to (4), wherein the molecule is present in an aqueous solution with pH higher than 7, preferably higher than 8.

(8) A composition according to paragraph (7), wherein the molecule is present in a clear solution with pH equal or higher than 10.

(9) A composition according to any one of paragraphs (1) to (4), wherein the particles of the molecule are present in an aqueous suspension or gel.

(10) A composition according to paragraphs (9), wherein the particles of the molecule are present in an aqueous suspension or gel with pH about 4-10.

(11) A composition according to any one of paragraphs (1) to (3), wherein the particles of the molecule are present in a non-aqueous medium.

(12) A composition according to any one of paragraphs (1) to (11), wherein the molecule is present in a concentration of about 0.001-500 mg/mL, preferable about 0.1-10 mg/mL.

(13) A composition according to any one of paragraphs (1) to (12), further comprising a preservative.

(14) A composition according to paragraph (13), wherein said preservative is selected from the group consisting of m-cresol, phenol, benzyl alcohol and methyl paraben.

(15) A composition according to paragraph (14), wherein said preservative is present in a concentration from 0.01 mg/mL to 50 mg/mL.

(16) A composition according to any one of paragraphs (1) to (15), further comprising an isotonic agent.

(17) A composition according to paragraphs (1) to (16), wherein said isotonic agent is present in a concentration from 0.01 mg/mL to 50 mg/mL.

(18) A composition according to any one of paragraphs (1) to (17), further comprising Aa divalent ion, preferably zinc.

(19) A composition according to paragraph (18), wherein said zinc is present in a concentration from 0.0005 mg/mL to 50 mg/mL.

(20) A composition according to any one of paragraphs (1) to (19), further comprising a stabilizer.

(21) A composition according to paragraph (20), wherein said stabilizer is selected from the group consisting of imidazole, arginine and histidine.

(22). A composition according to any one of paragraphs (1) to (21), further comprising a surfactant.

(23) A composition according to any one of paragraphs (1) to (22), further comprising a chelating agent.

(24) A composition according to any one of paragraphs (1) to (23), further comprising a buffer.

(25) A composition according to paragraph (24), wherein said buffer is selected from the group consisting of Tris, ammonium acetate, sodium acetate, glycine, aspartic acid, and Bis-Tris.

(26) A composition according to any one of paragraphs (1) to (25), further comprising a basic polypeptide.

(27) A composition according to paragraphs (26), wherein said basic polypeptide is selected from the group consisting of polylysine, polyarginine, polyornithine, protamine, putrescine, spermine, spermidine, and histone.

(28) A composition according to any one of paragraphs (1) to (27), further comprising alcohol or mono or disaccharide.

(29) A composition according to paragraph (28), wherein said alcohol or mono or disaccharide is selected from the group consisting of methanol, ethanol, propanol, glycerol, trehalose, mannitol, glucose, erythrose, ribose, galactose, fructose, maltose, sucrose, and lactose.

(30) A composition according to any one of paragraphs (1) to (29), further comprising ammonium sulfate.

(31) The composition of any one of paragraphs (1) to (30), wherein the molecule is selected from the group consisting of GLP-1 analogs and derivatives that have at least two residues selected from the group consisting of L- or D-Arg and L- or D-hArg.

(32) The composition of paragraph (31), wherein the molecule is selected from the group consisting of GLP-1 analogs and derivatives, wherein at least one of residues 26 and 34 is L- or D-Arg or L- or D-hArg.

(33) The composition of paragraph (32), wherein the said GLP-1 analog is a compound according to formula (I)

$$H-A^7-A^8-A^9-A^{10}-A^{11}-A^{12}-A^{13}-A^{14}-A^{15}-A^{16}-A^{17}-$$
$$A^{18}-A^{19}-A^{20}-A^{21}-A^{22}-A^{23}-A^{24}-A^{25}-A^{26}-A^{27}-$$
$$A^{28}-A^{29}-A^{30}-A^{31}-A^{32}-A^{33}-A^{34}-A^{35}-A^{36}-A^{37}-R^1, \quad (I)$$

wherein:

$A^7$ is L-His or deleted;
$A^8$ is Ala, D-Ala, Aib, Gly, Ser, Gly, β-Ala, Val, Acc, N-Me-Ala, N-Me-D-Ala or N-Me-Gly;
$A^9$ is Glu, N-Me-Glu, N-Me-Asp or Asp;
$A^{10}$ is Gly, Acc, β-Ala or Aib;
$A^{11}$ is Thr or Ser;
$A^{12}$ is Phe, Acc, Aic, Aib, 3Pal, 4Pal, 1Nal, 2Nal, Cha, Trp or $(X^1)_n$-Phe;
$A^{13}$ is Thr or Ser;
$A^{14}$ is Ser or Aib;
$A^{15}$ is Asp or Glu;
$A^{16}$ is Val, Acc, Aib, Leu, Ile, Tle, Nle, Abu, Ala, 1Nal, 2Nal or Cha;
$A^{17}$ is Ser or Thr;
$A^{18}$ is Ser or Thr;
$A^{19}$ is Tyr, Cha, Phe, 3Pal, 4Pal, Acc, 1Nal, 2Nal or $(X^1)_n$-Phe;
$A^{20}$ is Leu, Acc, Aib, Nle, Ile, Cha, Tle, Val, Phe, 1Nal, 2Nal or $(X^1)_n$-Phe;
$A^{21}$ is Glu or Asp;
$A^{22}$ is Gly, Acc, β-Ala or Aib;
$A^{23}$ is Gln or Asn;
$A^{24}$ is Ala, Aib, Val, Abu, Tle or Acc;
$A^{25}$ is Ala, Aib, Val, Abu, Tle or Acc;
$A^{26}$ is Lys, Arg, hArg, Orn, Dab, or Dap;
$A^{27}$ is Glu or Asp;

A²⁸ is Phe, 3Pal, 4Pal, 1Nal, 2Nal, Aic, Acc, Aib, Cha, Trp or $(X^1)_n$-Phe;
A²⁹ is Ile, Acc, Aib, Leu, Nle, Cha, Tle, Val, Abu, Ala, Phe, 1Nal, 2Nal or $(X^1)_n$-Phe;
A³⁰ is Ala, Aib or Acc;
A³¹ is Trp, 2Nal, 3Pal, 4Pal, Phe, Acc, Aib, Cha or $(X^1)_n$-Phe;
A³² is Leu, Acc, Aib, Nle, Ile, Cha, Tle, 1Nal, 2Nal, Phe, $(X^1)_n$-Phe or Ala;
A³³ is Val, Acc, Aib, Leu, Ile, Tle, Nle, Cha, Ala, 1Nal, 2Nal, Phe, Abu, Lys or $(X^1)_n$-Phe;
A³⁴ is Lys, Arg, hArg, Orn, Dab or Dap;
A³⁵ is Gly, β-Ala, Gaba, Ava, HN—$(CH_2)_m$—C(O), Aib, Acc, a D-amino acid, or deleted;
A³⁶ is L- or D-Arg, D- or L-Lys, D- or L-hArg, D- or L-Orn, L- or D-Dab, L- or D-Dap, or deleted; and
A³⁷ is Gly, β-Ala, Gaba, Ava, Aib, Acc, Ado, Aun, Aec, a D-amino acid, or deleted;
$X^1$ for each occurrence is independently for each occurrence $(C_1-C_6)$alkyl, OH or halogen;
n is 1, 2, 3, 4, or 5;
$R^1$ is OH, $NH_2$, $(C_1-C_{30})$alkoxy, or NH—$X^2$—$CH_2$—$Z^0$, wherein $X^2$ is a $(C_1-C_{12})$hydrocarbon moiety, and $Z^0$ is H, OH, $CO_2H$ or $CONH_2$;

(34) A composition according to paragraph (33), wherein said GLP-1 analog is a compound according to formula:
(Aib⁸, Arg²⁶)hGLP-1(7-36)NH₂;
(Aib⁸, Arg²⁶, Phe³¹-Ala35)hGLP-1(7-36)NH₂;
(Aib⁸, Arg²⁶, β-Ala³⁵)hGLP-1(7-36)NH₂;
(Aib⁸, Arg²⁶,³⁴)hGLP-1(7-36)NH₂;
(Aib⁸, Arg²⁶,³⁴, β-Ala³⁵)hGLP-1(7-36)NH₂;
(Aib⁸, Arg³⁴)hGLP-1(7-36)NH₂;
(Aib⁸, Arg³⁴, Phe³¹, β-Ala³⁵)hGLP-1(7-36)NH₂;
(Aib⁸,³⁵, Arg³⁴, β-Ala³⁵)hGLP-1(7-36)NH₂;
(Aib⁸,³⁵, 1Nal¹², Arg²⁶,³⁴)hGLP-1(7-36)NH₂;
(Aib⁸,³⁵, 1Nal¹², Arg²⁶,³⁴, Phe³¹)hGLP-1(7-36)NH₂;
(Aib⁸,³⁵, 1Nal¹²,³¹, Arg²⁶,³⁴)hGLP-1(7-36)NH₂;
(Aib⁸,³⁵, 1Nal¹⁹, Arg²⁶,³⁴)hGLP-1(7-36)NH₂;
(Aib⁸,³⁵, 1Nal¹⁹, Arg²⁵,³⁴, Phe³¹)hGLP-1(7-36)NH₂;
(Aib⁸,³⁵, 1Nal¹⁹,³¹, Arg²⁶,³⁴)hGLP-1(7-36)NH₂;
(Aib⁸,³⁵, 2Nal¹², Arg²⁶,³¹)hGLP-1(7-36)NH₂;
(Aib⁸,³⁵, 2Nal¹², Arg²⁶,³¹, Phe³⁴)hGLP-1(7-36)NH₂;
(Aib⁸,³⁵, 2Nal¹²,³¹, Arg²⁶,³⁴)hGLP-1(7-36)NH₂;
(Aib⁸,³⁵, 2Nal¹⁹, Arg²⁶,³⁴)hGLP-1(7-36)NH₂;
(Aib⁸,³⁵, 2Nal¹⁹, Arg²⁶,³⁴, Phe³¹)hGLP-1(7-36)NH₂;
(Aib⁸,³⁵, 2Nal¹⁹,³¹, Arg²⁶,³⁴)hGLP-1(7-36)NH₂;
(Aib⁸,³⁵, Arg²⁶)hGhLP-1(7-36)NH₂;
(Aib⁸,³⁵, Arg²⁶, Phe³¹)hGLP-1(7-36)NH₂;
(Aib⁸,³⁵, Arg²⁶,³⁴)hGLP-1(7-36)NH₂;
(Aib⁸,³⁵, Arg²⁶,³⁴, 1Nal²⁸)hGLP-1(7-36)NH₂;
(Aib⁸,³⁵, Arg²⁶,³⁴, 1Nal²⁸, Phe³¹)hGLP-1(7-36)NH₂;
(Aib⁸,³⁵, Arg²⁶,³⁴, 1Nal²⁶,³¹)hGLP-1(7-36)NH₂;
(Aib⁸,³⁵, Arg²⁶,³⁴, 1Nal³¹)hGLP-1(7-36)NH₂;
(Aib⁸,³⁵, Arg²⁶,³⁴, 2Nal²⁸)hGLP-1(7-36)NH₂;
(Aib⁸,³⁵, Arg²⁶,³⁴, 2Nal²⁸, Phe³¹)hGLP-1(7-36)NH₂;
(Aib⁸,³⁵, Arg²⁶,³⁴, 2Nal²⁸,³¹)hGLP-1(7-36)NH₂;
(Aib⁸,³⁵, Arg²⁶,³⁴, 2Nal³¹)hGLP-1(7-36)NH₂;
(Aib⁸,³⁵, Arg²⁶,³⁴, Phe³⁴)hGLP-1(7-36)NH₂;
(Aib⁸,³⁵, Arg³⁴)hGLP-1(7-36)NH₂;
(Aib⁸,³⁵, Phe³¹, Arg³⁴)hGLP-1(7-36)NH₂;
(Arg²⁶)hGLP-1(7-36)NH₂;
(Arg²⁶, Aib³⁵)hGLP-1(7-36)NH₂;
(Arg²⁶, β-Ala³⁵)hGLP-1(7-36)NH₂;
(Arg²⁶,³⁴)hGLP-1(7-36)NH₂;
(Arg²⁶,³⁴, Aib³⁵)hGLP-1(7-36)NH₂;
(Arg²⁶,³⁴, β-Ala³⁵)hGLP-1(7-36)NH₂;
(Arg³⁴)hGLP-1(7-36)NH₂;
(Arg³⁴, Aib³⁵)hGLP-1(7-36)NH₂;
(Arg³⁴, β-Ala³⁵)hGLP-1(7-36)NH₂;
(D-Ala⁸, Arg²⁶)hGLP-1(7-36)NH₂;
(D-Ala⁸, Arg²⁶, Aib³⁵)hGLP-1(7-36)NH₂;
(D-Ala⁸, Arg²⁶, β-Ala³⁵)hGLP-1(7-36)NH₂;
(D-Ala⁸, Arg²⁶,³⁴)hGLP-1(7-36)NH₂;
(D-Ala⁸, Arg²⁶,³⁴, Aib³⁵)hGLP-1(7-36)NH₂;
(D-Ala⁸, Arg²⁶,³⁴, β-Ala³⁵)hGLP-1(7-36)NH₂;
(D-Ala⁸, Arg³⁴)hGLP-1(7-36)NH₂;
(D-Ala⁸, Arg³⁴, Aib³⁵)hGLP-1(7-36)NH₂;
(D-Ala⁸, Arg³⁴, β-Ala³⁵)hGLP-1(7-36)NH₂;
(Gly⁸, Arg²⁶)hGLP-1(7-36)NH₂;
(Gly⁸, Arg²⁶, Aib³⁵)hGLP-1(7-36)NH₂;
(Gly⁸, Arg²⁶, β-Ala³⁵)hGLP-1(7-36)NH₂;
(Gly⁸, Arg²⁶,³⁴)hGLP-1(7-36)NH₂;
(Gly⁸, Arg²⁶,³⁴, Aib³⁵)hGLP-1(7-36)NH₂;
(Gly⁸, Arg²⁶,³⁴, β-Ala³⁵)hGLP-1(7-36)NH₂;
(Gly⁸, Arg³⁴)hGLP-1(7-36)NH₂;
(Gly⁸, Arg³⁴, Aib³⁵)hGLP-1(7-36)NH₂;
(Gly⁸, Arg³⁴, β-Ala³⁵)hGLP-1(7-36)NH₂;
(N-Me-D-Ala⁸, Arg²⁶,³⁴)hGLP-1(7-36)NH₂;
(N-Me-D-Ala⁸, Arg²⁶,³⁴, Aib³⁵)hGLP-1(7-36)NH₂;
(N-Me-D-Ala⁸, Arg²⁶,³⁴, β-Ala35)hGLP-1(7-36)NH₂,
(Ser⁸, Arg²⁶)hGLP-1(7-36)NH₂;
(Ser⁸, Arg²⁶, Aib³⁵)hGLP-1(7-36)NH₂;
(Ser⁸, Arg²⁶, β-Ala³⁵)hGLP-1(7-36)NH₂;
(Ser⁸, Arg²⁶,³⁴)hGLP-1(7-36)NH₂;
(Ser⁸, Arg²⁶,³⁴, Aib³⁵)hGLP-1(7-36)NH₂;
(Ser⁸, Arg²⁶,³⁴, β-Ala³⁵)hGLP-1(7-36)NH₂;
(Ser⁸, Arg³⁴)hGLP-1(7-36)NH₂;
(Ser⁸, Arg³⁴, Aib³⁵)hGLP-1(7-36)NH₂;
(Ser⁸, Arg³⁴, β-Ala³⁵)hGLP-1(7-36)NH₂;
(Val⁸, Arg²⁶)hGLP-1(7-36)NH₂,
(Val⁸, Arg²⁶, Aib³⁵)hGLP-1(7-36)NH₂,
(Val⁸, Arg²⁶, β-Ala³⁵)hGLP-1(7-36)NH₂,
(Val⁸, Arg²⁶,³⁴)hGLP-1(7-36)NH₂;
(Val⁸, Arg²⁶,³⁴, Aib³⁵)hGLP-1(7-36)NH₂;
(Val⁸, Arg²⁶,³⁴, β-Ala³⁵)hGLP-1(7-36)NH₂;
(Val⁸, Arg³⁴)hGLP-1(7-36)NH₂;
(Val⁸, Arg³⁴, Aib³⁵)hGLP-1(7-36)NH₂; or
(Val⁸, Arg³⁴, β-Ala³⁵)hGLP-1(7-36)NH₂.

(35) In a more preferred embodiment the invention features a composition according to paragraph (34), wherein said GLP-1 analog is a compound according to the formula:
(Aib⁸, Arg²⁶,³⁴, β-Ala³⁵)hGLP-1(7-36)NH₂;
(Aib⁸,³⁵, Arg²⁶)hGLP-1(7-36)NH₂;
(Aib⁸,³⁵, Arg²⁶, Phe³¹)hGLP-1(7-36)NH₂;
(Aib⁸,³⁵, Arg²⁶,³⁴)hGLP-1(7-36)NH₂;
(Aib⁸,³⁵, Arg²⁶,²⁴, 2Nal³¹)hGLP-1(7-36)NH₂;
(Aib⁸,³⁵, Arg²⁶,³⁴, Phe³¹)hGLP-1(7-36)NH₂;
(Aib⁸,³⁵, Arg³⁴)hGLP-1(7-36)NH₂;
(Aib⁸,³⁵, Phe³¹, Arg³⁴)hGLP-1(7-36)NH₂;

(36) In a still more preferred embodiment the invention features a composition according to paragraph (34), wherein said GLP-1 analog is a compound according to the formula:

(Aib⁸,³⁵, Arg²⁶,³⁴, Phe³¹)hGLP-1(7-36)NH₂.

(37) A method of eliciting an agonist effect from a GLP-1 receptor in a subject in need thereof which comprises administering to said subject an effective amount of a compound according to paragraph (1) or paragraph (33), or a pharmaceutically acceptable salt thereof.

(38) A method of treating a disease selected from the group consisting of Type I diabetes, Type II diabetes, obesity, glucagonomas, secretory disorders of the airway, metabolic disorder, arthritis, osteoporosis, central nervous system disease, restenosis and neurodegenerative disease, in a subject in need thereof which comprises administering to said subject an effective amount of a composition according to paragraph (1) or a pharmaceutically acceptable salt thereof. Preferably said disease is Type I diabetes or Type II diabetes.

(39) Another more preferred compound of formula (I) for use in a formulation of the present invention is each of the compounds that are specifically exemplified hereinbelow in the Examples section of the present disclosure, or a pharmaceutically acceptable salt thereof.

(40). In yet another aspect, the present invention provides a method of eliciting an agonist effect from a GLP-1 receptor in a subject in need thereof which comprises administering to said subject a formulation of the instant present invention comprising an effective amount of a compound of formula (I) as defined hereinabove or a pharmaceutically acceptable salt thereof.

(41) In a further aspect, the present invention provides a method of treating a disease selected from the group consisting of Type I diabetes, Type II diabetes, obesity, glucagonomas, secretory disorders of the airway, metabolic disorder, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake is desired, in a subject in need thereof which comprises administering to said subject for use in a formulation of the present invention comprising an effective amount of a compound of formula (I) as defined hereinabove or a pharmaceutically acceptable salt thereof. A preferred method of the immediately foregoing method is where the disease being treated is Type I diabetes or Type II diabetes.

(42) In a still more preferred aspect, the invention features a method according to paragraphs (40) or (41) wherein said composition comprises and aqueous solution consisting essentially of a salt of [Aib$^{8,35}$, Arg$^{26,34}$, Phe$^{31}$]hGLP-1(7-36)NH$_2$ and a salt of zinc, more preferably wherein the pH of said composition is lower than 7.0, more preferably still, lower than 5.0, more preferably still, lower than 4.0.

(43) In a more preferred embodiment the invention features a composition of paragraph wherein the concentration of [Aib$^{8,35}$, Arg$^{26,34}$, Phe$^{31}$]hGLP-1(7-36)NH$_2$ is 0.5 to 8.0 mg/ml, more preferably about 2.0 to about 6.0 mg/ml, more preferably still about 3.5 to 5.5 mg/ml., even more preferably still about 4.0 mg/ml.

(44) Further preferred embodiments of the invention are described in following paragraphs (45) to (77):

(45) A pharmaceutical composition of a clear solution or a gel comprising zinc and an analog of GLP-1 or exendin-4.

(46) A pharmaceutical composition according to paragraph (45), wherein said composition forms a precipitate after subcutaneous administration to a subject.

(47) A composition according to paragraph (46), further comprising water.

(48) A composition according to any one of paragraphs (46) and (47), further comprising non-aqueous medium.

(49) A composition according to any one of paragraphs (47)-(48), wherein the molecule is present in an aqueous solution with pH between 2.5 and 10.5, preferably between 3.5 and 8.

(50) A composition according to any one of paragraphs (46-49), wherein the molecule is present in a concentration of about 0.001-500 mg/mL, preferable about 0.1-10 mg/mL.

(51) A composition according to any one of paragraphs (46-50), further comprising a preservative.

(52) A composition according to paragraph (51), wherein said preservative is selected from the group consisting of m-cresol, phenol, benzyl alcohol and methyl paraben.

(53) A composition according to paragraph (52), wherein said preservative is present in a concentration from 0.01 mg/mL to 50 mg/mL.

(54) A composition according to any one of paragraphs (45-53), further comprising an isotonic agent.

(55) A composition according to paragraph (54), wherein said isotonic agent is present in a concentration from 0.01 mg/mL to 50 mg/mL.

(56) A composition according to any one of paragraphs (46-55), wherein said zinc is present in a concentration from 0.0005 mg/mL to 50 mg/mL.

(57) A composition according to any one of paragraphs (46-56), further comprising a stabilizer.

(58) A composition according to paragraph (57), wherein said stabilizer is selected from the group consisting of imidazole, arginine and histidine.

(59) A composition according to any one of paragraphs (46-58), further comprising a surfactant.

(60) A composition according to any one of paragraphs (46-59), further comprising a chelating agent.

(61) A composition according to any one of paragraphs (46-60), further comprising a buffer.

(62) A composition according to paragraph (61), wherein said buffer is selected from the group consisting of Tris, ammonium acetate, sodium acetate, glycine, aspartic acid, and Bis-Tris.

(63) A composition according to any one of paragraphs (46-62), further comprising a basic polypeptide.

(64) A composition according to paragraph (63), wherein said basic polypeptide is selected from the group consisting of polylysine, polyarginine, polyornithine, protamine, putrescine, spermine, spermidine, and histone.

(65) A composition according to any one of paragraphs (46-64), further comprising alcohol or mono or disaccharide.

(66) A composition according to paragraph (65), wherein said alcohol or mono or disaccharide is selected from the group consisting of methanol, ethanol, propanol, glycerol, trehalose, mannitol, glucose, erythrose, ribose, galactose, fructose, maltose, sucrose, and lactose.

(67) A composition according to any one of paragraphs (46-66), comprising (Aib$^{8,35}$, Arg$^{26,34}$, Phe$^{3}$ )hGLP-1(7-36)NH$_2$; or a pharmaceutically acceptable salt thereof.

(68) A pharmaceutical composition consisting essentially of an analog according to the formula [Aib$^{8}$35, Arg$^{26}$34, Phe$^{31}$]hGLP-1(7-36)NH$_2$, or a pharmaceutically acceptable salt thereof.

(69) A pharmaceutical composition according to paragraph 68 in the form of a solid microtablet.

(70) A pharmaceutical composition according to paragraph 68, further comprising water, wherein said composition forms a semi-solid.

(71) A pharmaceutical semi-solid composition according to paragraph 70, wherein said composition contains approximately 25% (wt/wt) of (Aib$^{8,35}$, Arg$^{26,34}$, Phe$^{31}$)hGLP-1(7-36)NH$_2$.

(72) A pharmaceutical composition comprising an analog according to the formula:

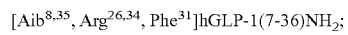

or

together with zinc and a pharmaceutically acceptable carrier or diluent.

(73) A composition according to paragraph 72, wherein said zinc is present in a concentration from 0.0005 mg/mL to 50 mg/mL.

(74) A composition according to paragraph 73, wherein said zinc is present in a concentration from 0.01 mg/mL to 0.50 mg/mL.

(75) A composition according to paragraph 72, wherein said diluent comprises a pharmaceutically acceptable aqueous solution.

(76) A composition according to paragraph 75, wherein said diluent comprises sterile water.

(77) A method of treating a disease selected from the group consisting of Type I diabetes, Type II diabetes, obesity, glucagonomas, secretory disorders of the airway, metabolic disorder, arthritis, osteoporosis, central nervous system disease, restenosis, neurodegenerative disease, renal failure, congestive heart failure, nephrotic syndrome, cirrhosis, pulmonary edema, hypertension, and disorders wherein the reduction of food intake is desired, in a subject in need thereof which comprises administering to said subject a formulation selected, independently for each occurrence, from the list of formulations comprising those described in each of paragraphs (43) and (45) - (76). A preferred method of the immediately foregoing method is where the disease being treated is Type I diabetes or Type II diabetes.

With the exception of the N-terminal amino acid, all abbreviations (e.g. Ala) of amino acids in this disclosure stand for the structure of —NH—CH(R)—CO—, wherein R is the side chain of an amino acid (e.g., $CH_3$ for Ala). For the N-terminal amino acid, the abbreviation stands for the structure of $(R^2R^3)$—N—CH(R)—CO—, wherein R is a side chain of an amino acid and $R^2$ and $R^3$ are as defined above, except when $A^7$ is Ura, Paa or Pta, in which case $R^2$ and $R^3$ are not present since Ura, Paa and Pta are considered here as des-amino amino acids. Amp, 1Nal, 2Nal, Nle, Cha, 3-Pal, 4-Pal and Aib are the abbreviations of the following (α-amino acids: 4-amino-phenylalanine, β-(1-naphthyl)alanine, β-(2-naphthyl)alanine, norleucine, cyclohexylalanine, β-(3-pyridinyl) alanine, β-(4-pyridinyl)alanine and (α-aminoisobutyric acid, respectively. Other amino acid definitions are: Ura is urocanic acid; Pta is (4-pyridylthio) acetic acid; Paa is trans-3-(3-pyridyl) acrylic acid; Tma-His is N,N-tetramethylamidino-histidine; N-Me-Ala is N-methyl-alanine; N-Me-Gly is N-methyl-glycine; N-Me-Glu is N-methyl-glutamic acid; Tle is tert-butylglycine; Abu is a-aminobutyric acid; Tba is tert-butylalanine; Orn is ornithine; Aib is α-aminoisobutyric acid; β-Ala is β-alanine; Gaba is γ-aminobutyric acid; Ava is 5-aminovaleric acid; Ado is 12-aminododecanoic acid, Aic is 2-aminoindane-2-carboxylic acid; Aun is 11-aminoundecanoic acid; and Aec is 4-(2-aminoethyl)-1-carboxymethyl-piperazine, represented by the structure:

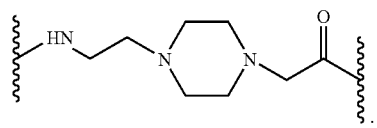

What is meant by Acc is an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c). In the above formula, hydroxyalkyl, hydroxyphenylalkyl, and hydroxynaphthylalkyl may contain 14 hydroxy substituents. $COX^5$ stands for —C=O.$X^5$. Examples of —C=O.$X^5$ include, but are not limited to, acetyl and phenylpropionyl.

The full names for other abbreviations used herein are as follows: Boc for t-butyloxycarbonyl, HF for hydrogen fluoride, Fm for formyl, Xan for xanthyl, Bzl for benzyl, Tos for tosyl, DNP for 2,4-dinitrophenyl, DMF for dimethylformamide, DCM for dichloromethane, HBTU for 2-(1H-Benzotriazol-1-yl)-1,1,3,3-tetramethyl uronium hexafluorophosphate, DIEA for diisopropylethylamine, HOAc for acetic acid, TFA for trifluoroacetic acid, 2ClZ for 2-chlorobenzyloxycarbonyl, 2BrZ for 2-bromobenzyloxycarbonyl, OcHex for O-cyclohexyl, Fmoc for 9-fluorenylmethoxycarbonyl, HOBt for N-hydroxybenzotriazole; PAM resin for 4-hydroxymethylphenylacetamidomethyl resin; Tris for Tris(hydroxymethyl)aminomethane; and Bis-Tris for Bis(2-hydroxyethyl)amino-tris(hydroxymethyl)methane (i.e., 2-Bis (2-hydroxyethyl)amino-2-(hydroxymethyl)-1,3-propanediol).

The term "halo" or "halogen" encompasses fluoro, chloro, bromo and iodo.

The terms "$(C_1-C_{12})$hydrocarbon moiety", "$(C_1-C_{30})$hydrocarbon moiety" and the like encompass branched and straight chain alkyl, alkenyl and alkynyl groups having the indicated number of carbons, provided that in the case of alkenyl and alkynyl there is a minimum of two carbons.

A peptide of this invention is also denoted herein by another format, e.g., $(A5c^8)$hGLP-1(7-36)$NH_2$, with the substituted amino acids from the natural sequence placed between the first set of parentheses (e.g., $A5c^8$ for $Ala^8$ in hGLP-1). The abbreviation GLP-1 means glucagon-like peptide-1; hGLP-1 means human glucagon-like peptide-1. The numbers between the parentheses refer to the number of amino acids present in the peptide (e.g., hGLP-1(7-36) is amino acids 7 through 36 of the peptide sequence for human GLP-1). The sequence for hGLP-1 (7-37) is listed in Mojsov, S., Int. J. Peptide Protein Res,. 40,1992, pp. 333-342. The designation "$NH_2$" in hGLP-1 (7-36)$NH_2$ indicates that the C-terminus of the peptide is amidated. hGLP-1(7-36) means that the C-terminus is the free acid. In hGLP-1(7-38), residues in positions 37 and 38 are Gly and Arg, respectively, unless otherwise indicated.

DETAILED DESCRIPTION

Synthesis of Peptides

Figure 1:
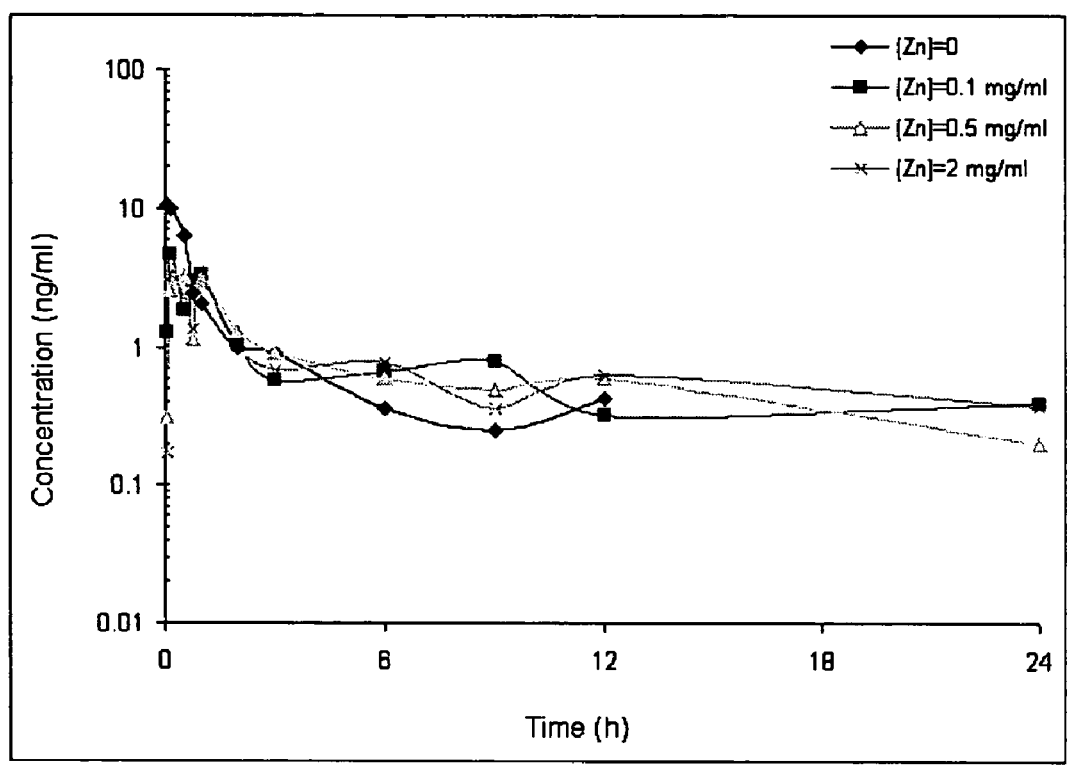
FIG. 1 depicts the time course plasma concentration of a peptide administered to rats using compositions according to the invention, according to Example H.1.

Peptides useful for practicing the present invention can be and were prepared by standard solid phase peptide synthesis. See, e.g., Stewart, J. M., et al., Solid Phase Synthesis (Pierce Chemical Co., 2d ed. 1984). The substituents $R^2$ and $R^3$ of the above generic formula may be attached to the free amine of the N-terminal amino acid by standard methods known in the art. For example, alkyl groups, e.g., ($C_1$-$C_{30}$)alkyl, may be attached using reductive alkylation. Hydroxyalkyl groups, e.g., ($C_1$-$C_{30}$)hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for one hour. If the free acid contains a free hydroxy group, e.g., p-hydroxyphenylpropionic acid, then the coupling should be performed with an additional 3 molar equivalents of HOBT.

When $R^1$ is NH—$X^2$—$CH_2$—$CONH_2$, (i.e., $Z^0$=$CONH_2$), the synthesis of the peptide starts with BocHN-$X^2$—$CH_2$—COOH which is coupled to the MBHA resin. If $R^1$ is NH—$X^2$—$CH_2$—COOH, (i.e., $Z^0$=COOH) the synthesis of the peptide starts with Boc-HN—$X^2$—$CH_2$—COOH which is coupled to PAM resin. For this particular step, 4 molar equivalents of Boc-HN—$X^2$—COOH, HBTU and HOBt and 10 molar equivalents of DIEA are used. The coupling time is about 8 hours.

The protected amino acid 1-(N-tert-butoxycarbonyl-amino)-1-cyclohexane-carboxylic acid (Boc-A6c-OH) was synthesized as follows. 19.1 g (0.133 mol) of 1-amino-1-cyclohexanecarboxylic acid (Acros Organics, Fisher Scientific, Pittsburgh, Pa.) was dissolved in 200 ml of dioxane and 100 ml of water. To it was added 67 ml of 2N NaOH. The solution was cooled in an ice-water bath. 32.0 g (0.147 mol) of di-tert-butyl-dicarbonate was added to this solution. The reaction mixture was stirred overnight at room temperature. Dioxane was then removed under reduced pressure. 200 ml of ethyl acetate was added to the remaining aqueous solution. The mixture was cooled in an ice-water bath. The pH of the aqueous layer was adjusted to about 3 by adding 4N HCl. The organic layer was separated. The aqueous layer was extracted with ethyl acetate (1×100 ml). The two organic layers were combined and washed with water (2×150 ml), dried over anhydrous $MgSO_4$, filtered, and concentrated to dryness under reduced pressure. The residue was recrystallized in ethyl acetate/hexanes. 9.2 g of the pure product was obtained. 29% yield.

Boc-A5c-OH was synthesized in an analogous manner to that of Boc-A6c-OH. Other protected Acc amino acids can be prepared in an analogous manner by a person of ordinary skill in the art as enabled by the teachings herein.

In the synthesis of a peptide containing A5c, A6c and/or Aib, the coupling time is 2 hrs. for these residues and the residue immediately following them. For the synthesis of (Tma-His[7])hGLP-1(7-36)$NH_2$, HBTU (2 mmol) and DIEA (1.0 ml) in 4 ml DMF are used to react with the N-terminal free amine of the peptide-resin in the last coupling reaction; the coupling time is about 2 hours.

The substituents $R^2$ and $R^3$ of the above generic formula can be attached to the free amine of the N-terminal amino acid by standard methods known in the art. For example, alkyl groups, e.g., ($C_1$-$C_{30}$)alkyl, can be attached using reductive alkylation. Hydroxyalkyl groups, e.g., ($C_1$-$C_{30}$)hydroxyalkyl, can also be attached using reductive alkylation wherein the free hydroxy group is protected with a t-butyl ester. Acyl groups, e.g., $COX^1$, can be attached by coupling the free acid, e.g., $X^1COOH$, to the free amine of the N-terminal amino acid by mixing the completed resin with 3 molar equivalents of both the free acid and diisopropylcarbodiimide in methylene chloride for about one hour. If the free acid contains a free hydroxy group, e.g., p-hydroxyphenylpropionic acid, then the coupling should be performed with an additional 3 molar equivalents of HOBT.

The following examples describe synthetic methods that can be and were used for making peptides with which the instant invention may advantageously be practiced, which synthetic methods are well-known to those skilled in the art. Other methods are also known to those skilled in the art. The examples are provided for the purpose of illustration and is not meant to limit the scope of the present invention in any manner.

Boc-βAla-OH, Boc-D-Arg(Tos)-OH and Boc-D-Asp (OcHex) were purchased from Nova Biochem, San Diego, Calif. Boc-Aun-OH was purchased from Bachem, King of Prussia, Pa. Boc-Ava-OH and Boc-Ado-OH were purchased from Chem-Impex International, Wood Dale, Ill. Boc-2Nal-OH was purchased from Synthetech, Inc. Albany, Oreg.

EXAMPLE 1

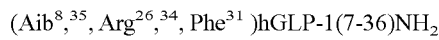
(Aib[8,35], Arg[26,34], Phe[31])hGLP-1(7-36)$NH_2$

The title peptide was synthesized on an Applied Biosystems (Foster City, Calif.) model 430A peptide synthesizer which was modified to do accelerated Boc-chemistry solid phase peptide synthesis. See Schnolzer, et al., Int. J. Peptide Protein Res., 90:180 (1992). 4-methylbenzhydrylamine (MBHA) resin (Peninsula, Belmont, Calif.) with the substitution of 0.91 mmol/g was used. The Boc amino acids (Bachem, Calif., Torrance, Calif.; Nova Biochem., LaJolla, Calif.) were used with the following side chain protection: Boc-Ala-OH, Boc-Arg(Tos)-OH, Boc-Asp(OcHex)-OH, Boc-Tyr(2BrZ)-OH, Boc-His(DNP)-OH, Boc-Val-OH, Boc-Leu-OH, Boc-Gly-OH, Boc-Gln-OH, Boc-Ile-OH, Boc-Lys (2ClZ)-OH, Boc-Thr(Bzl)-OH, Boc-Ser(Bzl)-OH, Boc-Phe-OH, Boc-Aib-OH, Boc-Glu(OcHex)-OH and Boc-Trp(Fm)-OH. The synthesis was carried out on a 0.20 mmol scale. The Boc groups were removed by treatment with 100% TFA for 2×1 min. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 min. except for the Boc-Aib-OH residues and the following residues, Boc-Lys (2ClZ)-OH and Boc-His(DNP)-OH wherein the coupling times were 2 hours.

At the end of the assembly of the peptide chain, the resin was treated with a solution of 20% mercaptoethanol/10% DIEA in DMF for 2×30 min. to remove the DNP group on the His side chain. The N-terminal Boc group was then removed by treatment with 100% TFA for 2×2 min. After neutralization of the peptide-resin with 10% DIEA in DMF (1×1 min), the formyl group on the side chain of Trp was removed by treatment with a solution of 15% ethanolamine/15% water/ 70% DMF for 2×30 min. The peptide-resin was washed with DMF and DCM and dried under reduced pressure. The final cleavage was done by stirring the peptide-resin in 10 mL of HF containing 1 mL of anisole and dithiothreitol (24 mg) at 0°

C. for 75 min. HF was removed by a flow of nitrogen. The residue was washed with ether (6×10 mL) and extracted with 4N HOAc (6×10 mL).

The peptide mixture in the aqueous extract was purified on reverse-phase preparative high pressure liquid chromatography (HPLC) using a reverse phase VYDAC® $C_{18}$ column (Nest Group, Southborough, Mass.). The column was eluted with a linear gradient (20% to 50% of solution B over 105 min.) at a flow rate of 10 mUmin (Solution A=water containing 0.1% TFA; Solution B=acetonitrile containing 0.1% of TFA). Fractions were collected and checked on analytical HPLC. Those containing pure product were combined and lyophilized to dryness. Approximately 18 mg of a white solid were obtained. Purity was 99% based on analytical HPLC analysis. Electro-spray mass spectrometer (MS(ES)) analysis gave the molecular weight at 3356.6 (in agreement with the calculated molecular weight of 3356.77).

The synthesis of Examples 2-82, as well as other peptidyl compounds useful to practice the present invention, can be accomplished in substantially the same manner as the procedure described for the synthesis of $(Aib^{8,35}, Arg^{26,34}, Phe^{31})$ hGLP-1(7-36)$NH_2$ in Example 1 above, but using the appropriate protected amino acids depending on the desired peptide.

EXAMPLES 2-82

Ex. No. Compound

2. $(Aib^8, Arg^{26})$hGLP-1(7-36)$NH_2$;
3. $(Aib^8, Arg^{26}, Phe^{31}, \beta\text{-Ala}^{35})$hGLP-1(7-36)$NH_2$;
4. $(Aib^8, Arg^{26}, \beta\text{-Ala}^{35})$hGLP-1(7-36)$NH_2$;
5. $(Aib^8, Arg^{26,34})$hGLP-1(7-36)$NH_2$;
6. $(Aib^8, Arg^{26,34}, \beta\text{-Ala}^{35})$hGLP-1(7-36)$NH_2$;
7. $(Aib^8, Arg^{34})$hGLP-1(7-36)$NH_2$;
8. $(Aib^8, Arg^{34}, Phe^{31}, \beta\text{-Ala}^{35})$hGLP-1(7-36)$NH_2$;
9. $(Aib^8, Arg^{34}, \beta\text{-Ala}^{35})$hGLP-1(7-36)$NH_2$;
10. $(Aib^{8,35}, 1Nal^{12}, Arg^{26,34})$hGLP-1(7-36)$NH_2$;
11. $(Aib^{8,35}, 1Nal^{12}, Arg^{26,34}, Phe^{31})$hGLP-1(7-36)$NH_2$;
12. $(Aib^{8,35}, 1Nal^{12,31}, Arg^{26,34})$hGLP-1(7-36)$NH_2$;
13. $(Aib^{8,35}, 1Nal^{91}, Arg^{26,34})$hGLP-1(7-36)$NH_2$;
14. $(Aib^{8,35}, 1Nal^{19}, Arg^{26,34}Phe^{31})$hGLP-1(7-36)$NH_2$;
15. $(Aib^{8,35}, 1Nal^{19,31}, Arg^{26,34})$hGLP-1(7-36)$NH_2$;
16. $(Aib^{8,35}, 2Nal^{12}, Arg^{26,34})$hGLP-1(7-36)$NH_2$;
17. $(Aib^{8,35}, 2Nal^{12}, Arg^{26,35}, Phe^{31})$hGLP-1(7-36)$NH_2$;
18. $(Aib^{8,35}, 2Nal^{12}, Arg^{26,35})$hGLP-1(7-36)$NH_2$;
19. $(Aib^{8,35}, 2Nal^{19}, Arg^{26,34})$hGLP-1(7-36)$NH_2$;
20. $(Aib^{8,35}, 2Nal^{19}, Arg^{26,34}, Phe^{31})$hGLP-1(7-36)$NH_2$;
21. $(Aib^{8,35}, 2Na^{19,31}, Arg^{26,34})$hGLP-1(7-36)$NH_2$;
22. $(Aib^{8,35}, Arg^{26})$hGLP-1(7-36)$NH_2$;
23. $(Aib^{8,35}, Arg^{26,34}, Phe^{31})$hGLP-1(7-36)$NH_2$;
24. $(Aib^{8,35}, Arg^{26,34})$hGLP-1(7-36)$NH_2$;
25. $(Aib^{8,35}, Arg^{26,34}, 1Nal^{28})$hGLP-1(7-36)$NH_2$;
26. $(Aib^{8,35}, Arg^{26,34}, 1Nal^{28}, Phe^{31})$hGLP-1(7-36)$NH_2$;
27. $(Aib^{8,35}, Arg^{26,34}, 1Nal^{28,31})$hGLP-1(7-36)$NH_2$;
28. $(Aib^{8,35}, Arg^{26,34}, 1Nal^{28})$hGLP-1(7-36)$NH_2$;
29. $(Aib^{8,35}, Arg^{26,34}, 2Nal^{28})$hGLP-1(7-36)$NH_2$;
30. $(Aib^{8,35}, Arg^{26,34}, 2Nal^{28}, Phe^{31})$hGLP-1(7-36)$NH_2$;
31. $(Aib^{8,35}, Arg^{26,34}, 2Nal^{28,31})$hGLP-1(7-36)$NH_2$;
32. $(Aib^{8,35}, Arg^{26,34}, 2Nal^{31})$hGLP-1(7-36)$NH_2$;
33. $(Aib^{8,35}, Arg^{34})$hGLP-1(7-36)$NH_2$;
34. $(Aib^{8,35}, Phe^{31}, Arg^{34})$hGLP-1(7-36)$NH_2$;
35. $(Arg^{26})$hGLP-1(7-36)$NH_2$;
36. $(Arg^{26}, Aib^{35})$hGLP-1(7-36)$NH_2$;
37. $(Arg^{26}, \beta\text{-Ala}^{35})$hGLP-1(7-36)$NH_2$;
38. $(Arg^{26,34})$hGLP-1(7-36)$NH_2$;
39. $(Arg^{26,34}, Aib^{35})$hGLP-1(7L36)$NHg$;
40. $(Arg^{26,34}, \beta\text{-Ala}^{35})$hGLP-1(7-36)$NH_2$;
41. $(Arg^{34})$hGLP-1(7-36)$NH_2$;
42. $(Arg^{34}, Aib^{35})$hGLP-1(7-36)$NH_2$;
43. $(Arg^{34}, \beta\text{-Ala})$hGLP-1(7-36)$NH_2$;
44. $(\text{D-Ala}^8, Arg^{26})$hGLP-1(7-36)$NH_2$;
45. $(\text{D-Ala}^8, Arg^{26}, Aib^{35})$hGLP-1(7-36)$NH_2$;
46. $(\text{D-Ala}^8, Arg^{26}, \beta\text{-Ala}^{35})$hGLP-1(7-36)$NH_2$;
47. $(\text{D-Ala}^8, Arg^{26,34})$hGLP-1(7-36)$NH_2$;
48. $(\text{D-Ala}^8, Arg^{26,34}, Aib^{35})$hGLP-1(7-36)$NH_2$;
49. $(\text{D-Ala}^8, Arg^{26,34}, Ala^{35})$hGLP-1(7-36)$NH_2$;
50. $(\text{D-Ala}^8, Arg^{34})$hGLP-1(7-36)$NH_2$;
51. $(\text{D-Ala}^8, Arg^{34}, Aib^{35})$hGLP-1(7-36)$NH_2$;
52. $(\text{D-Ala}^8, Arg^{34}, \beta\text{-Ala}^{35})$hGLP-1(7-36)$NH_2$;
53. $(Gly^8, Arg^{26})$hGLP-1(7-36)$NH_2$;
54. $(Gly^8, Arg^{26}, Aib^{35})$hGLP-1(7-36)$NH_2$;
55. $(Gly^8, Arg^{26}, \beta Ala^{35})$hGLP-1(7-36)$NH_2$;
56. $(Gly^8, Arg^{26,34})$hGLP-1(7-36)$NH_2$;
57. $(Gly^8, Arg^{26,34}, Aib^{35})$hGLP-1(7-36)$NH_2$;
58. $(Gly^8, Arg^{26,34}, Ala^{35})$hGLP-1(7-36)$NH_2$;
59. $(Gly^8, Arg^{34})$hGLP-1(7-36)$NH_2$;
60. $(Gly^8, Arg^{34}, Aib^{35})$hGLP-1(7-36)$NH_2$;
61. $(Gly^8, Arg^{34}, \beta\text{-Ala}^{35})$hGLP-1(7-36)$NH_2$;
62. $(\text{N-Me-D-Ala}^8, Arg^{26,34})$hGLP-1(7-36)$NH_2$;
63. $(\text{N-Me-D-Ala}^8, Arg^{26,34}, Aib^{35})$hGLP-1(7-36)$NH_2$;
64. $(\text{N-Me-D-Ala}^8, Arg^{26,34}, \beta\text{-Ala}^{35})$hGLP-1 (7-36)$NH_2$;
65. $(Ser^8, Arg^{26})$hGLP-1(7-36)$NH_2$;
66. $(Ser^8, Arg^{26}, Aib^{35})$hGLP-1(7-36)$NH_2$;
67. $(Ser^8, Arg^{26}, \beta\text{-Ala}^{35})$hGLP-1(7-36)$NH_2$;
68. $(Ser^8, Arg^{26,34})$hGLP-1(7-36)$NH_2$;
69. $(Ser^8, Arg^{26,34}, Aib^{35})$hGLP-1(7-36)$NH_2$;
70. $(Ser^8, Arg^{26,34}, \beta\text{-Ala}^{35})$hGLP-1(7-36)$NH_2$;
71. $(Ser^8, Arg^{34})$hGLP-1(7-36)$NH_2$;
72. $(Ser^8, Arg^{34}, Aib^{35})$hGLP-1(7-36)$NH_2$;
73. $(Ser^8, Arg^{34}, \beta\text{-Ala}^{35})$hGLP-1(7-36)$NH_2$;
74. $(Val^8, Arg^{26})$hGLP-1(7-36)$NH_2$;
75. $(Val^8, Arg^{26}, Aib^{35})$hGLP-1(7-36)$NH_2$;
76. $(Val^8, Arg^{26}, \beta\text{-Ala}^{35})$hGLP-1(7-36)$NH_2$;
77. $(Val^8, Arg^{26,34})$hGLP-1(7-36)$NH_2$;
78. $(Val^8, Arg^{26,34}, Aib^{35})$hGLP-1(7-36)$NH_2$;
79. $(Val^8, Arg^{26,34}, \beta\text{-Ala}^{35})$hGLP-1(7-36)$NH_2$;
80. $(Val^8, Arg^{34})$hGLP-1(7-36)$NH_2$;
81. $(Val^8, Arg^{34}, Aib^{35})$hGLP-1(7-36)$NH_2$;
82. $(Val^8, Arg^{34}, \beta\text{-Ala}^{35})$hGLP-1(7-36)$NH_2$.

Physical data for a representative sampling of the compounds exemplified herein are given in the following Table 1.

TABLE 1

| Ex. No. | Mol. Wt. Calculated | Mol. Wt. MS(ES) | Purity (HPLC) |
|---|---|---|---|
| 1 | 3356.77 | 3356.6 | 99% |
| 6 | 3381.74 | 3381.3 | 97% |
| 22 | 3367.75 | 3367.77 | 99% |
| 23 | 3328.72 | 3328.5 | 99% |
| 24 | 3395.74 | 3395.5 | 99% |
| 32 | 3406.84 | 3406.4 | 99% |
| 33 | 3367.75 | 3367.77 | 99% |
| 34 | 3328.72 | 3328.5 | 99% |

Experimental Procedures

A. Determination of GLP-1 Receptor Affinity

Compounds useful to practice the present invention can be tested for their ability to bind to the GLP-1 receptor using the following procedure.

Cell Culture:

RIN 5F rat insulinoma cells (ATCCO CRL-2058, American Type Culture Collection, Manassas, Va.), expressing the GLP-1 receptor, were cultured in Dulbecco's modified Eagle's medium (DMEM) containing 10% fetal calf serum, and maintained at about 37° C. in a humidifed atmosphere of 5% $CO_2$/95% air.

Radioligand Binding:

Membranes were prepared for radioligand binding studies by homogenization of the RIN cells in 20 ml of ice-cold 50 mM Tris-HCl with a Brinkman Polytron (Westbury, N.Y.) (setting 6, 15 sec). The homogenates were washed twice by centrifugation (39,000 g/10 min), and the final pellets were resuspended in 50 mM Tris-HCl, containing 2.5 mM $MgCl_2$, 0.1 mg/ml bacitracin (Sigma Chemical, St. Louis, Mo.), and 0.1% BSA. For assay, aliquots (0.4 ml) were incubated with 0.05 nM ($^{125}$I)GLP-1(7-36) (~2200 Ci/mmol, New England Nuclear, Boston, Mass.A), with and without 0.05 ml of unlabeled competing test peptides. After a 100 min incubation (25° C.), the bound ($^{125}$I)GLP-1(7-36) was separated from the free by rapid filtration through GF/C filters (Brandel, Gaithersburg, Md.), which had been previously soaked in 0.5% polyethyleneimine. The filters were then washed three times with 5 ml aliquots of ice-cold 50 mM Tris-HCl, and the bound radioactivity trapped on the filters was counted by gamma spectrometry (Wallac LKB, Gaithersburg, Md.). Specific binding was defined as the total ($^{125}$I)GLP-1(7-36) bound minus that bound in the presence of 1000 nM GLP1 (7-36) (Bachem, Torrence, Calif.).

B. Determination of Solubility vs pH

Advantageously, compounds for use in the present invention are relatively insoluble in aqueous solutions having approximately neutral or physiological pH values and relatively soluble in aqueous solutions having acidic or basic pH values. Preferably compounds for use in the present invention have an aqueous solubility lower than 1 mg/mL, more preferably lower than 0.5 mg/mL, at pH between approximately 6 and approximately 8 and at about temperatures between approximately 4° C. and approximately 40° C.

B.1. Determination of Compound Solubility vs pH in Buffered Saline

Compounds that may advantageously be used to practice the invention can be and were tested to determine their solubility in PBS at different pHs and temperatures using the following procedure.

A stock PBS buffered solution was made by dissolving one packet of pre-mixed powder (SIGMA, Product No.: P-3813) in one liter of de-ionized water to yield 10 mM phosphate-buffered saline with 138 mM NaCl, 2.7 mM KCl, and a pH of 7.4. PBS buffers with different pH values were made by adjusting the pH of this stock solution with phosphoric acid and/or sodium hydroxide.

2 mg samples of the compound of Example 1 were weighed into glass vials. Into each vial was added a 50 µl aliquot of PBS buffer at a certain pH. The solution was vortexed, and if necessary sonicated, until clear. For each pH tested the total volume of buffer needed to dissolve 2 mg of the compound was recorded and the solubility was calculated.

Peptide solutions that were clear at room temperature (20-25° C.) were placed in a refrigerator (4° C.) overnight and the solubility of the peptide at 4° C. was then examined.

B.2. Determination of Compound Solubility vs pH in Saline

Compounds that may advantageously be used to practice the invention can be and were tested to determine their solubility in saline at different pH values and temperatures using the following procedure.

A stock saline solution was prepared by dissolving 9 grams of NaCl in one liter of de-ionized water. Saline solutions with different pH values were made by adjusting the pH of this stock solution with HCl and/or NaOH.

2 mg samples of the compound of example 1 were weighed into glass vials. Into each vial was added a 50 µl aliquot of saline solution at a certain pH. The vial was vortexed and, if necessary, sonicated until clear. For each tested pH the total volume of saline needed to dissolve 2 mg of the compound was recorded and the solubility was calculated.

Solutions that were clear at room temperature (20-25° C.) were placed in a refrigerator (4° C.) overnight and the solubility at 4° C. then examined.

B.3. Determination of Compound Solubility in Saline at pH 7.0

Compounds that may advantageously be used to practice the invention can be and were tested to determine their solubility at room temperature in saline having pH=7 using the following procedure.

Saline solution was prepared by dissolving 9 grams of NaCl in one liter of de-ionized water. 2 mg each of ($Aib^8$, $Arg^{26,34}$, β-$Ala^{35}$)hGLP-1(7-36)$NH_2$ (example 6), ($Aib^{8,35}$, $Arg^{26,34}$)hGLP-1(7-36)$NH_2$ (example 24), and ($Aib^8 35$, $Arg^{26,34}$, $2Nal^{31}$)hGLP-1(7-36)$NH_2$ (example 32) were weighed into separate glass vials respectively and 1 mL aliquots of of saline were added, with vortexing and sonication, until clear. The total volume of saline used to dissolve 2 mg of peptide was recorded and the solubility at room temperature was calculated.

B.4. Determination of Compound Solubility in Saline at various pH

Compounds that may advantageously be used to practice the invention can be and were tested to determine their solubility at room temperature in saline solutions having various pH values using the following procedure.

A stock saline solution was prepared by dissolving 9 grams of NaCl in one liter of de-ionized water. Saline solutions having various pH values were obtained by treating aliquots of this stock saline solution with HCl and NaOH.

2 mg samples of ($Aib^{8,35}$, $Arg^2$, $Phe^3$)hGLP-1 (7-36)$NH_2$ (example 23) and of ($Aib^{8,35}$, $Phe^{31}$, $Arg^{34}$)hGLP-1(7-36)$NH_2$ (example 34) were weighed into glass vials, respectively. Aliquots of 50 µl of a saline buffer at a certain pH were added. The solution was vortexed and sonicated until clear. The total volume of buffer used to dissolve 2 mg of peptide was recorded and the solubility was calculated.

C. Determination of Aqueous Solubility of Compound vs Zinc Concentration

Compounds that may advantageously be used to practice the invention can be and were tested to determine their solubility in pH 7 water at different zinc concentrations using the following procedure.

A stock zinc solution was prepared by dissolving $ZnCl_2$ in de-ionized water to a concentration of 100 mg/ml and adjusting the pH to 2.7 using HCl. Solutions having various $ZnCl_2$ concentrations ("Zn Test Solutions") were prepared by making appropriate dilutions of the stock solution.

1 mg of the compound of Example 1 was dissolved in 250 µl of each Zn Test Solution to yield a solution having 4 mg/ml of the Example 1 compound. The pH of this solution was then adjusted using 0.2 N NaOH until white precipitates were observed to form. The precipitation solution was centrifuged and the mother liquor analyzed using HPLC. The UV absorption area of test compound peak was measured and the concentration of the test compound in the mother liquor was determined via comparison to a calibration curve.

As a representative example of a compound that may be used to practice the invention, the compound of Example 1 was tested in the immediately foregoing assay and the following results were obtained (aqueous saline, pH 7.0, room temperature):

TABLE 2

| $ZnCl_2$ concentration (µg/mL) | Solubility (mg/mL) |
| --- | --- |
| 0 | 0.0539 |
| 80 | 0.0059 |
| 500 | 0.0056 |
| 1000 | 0.0097 |
| 1500 | 0.0097 |
| 2500 | 0.0110 |

D. Preparation of Peptide/Zinc Solution Having pH=4.0

A 0.5 mg/ml $ZnCl_2$ solution was prepared by dilution of a solution of 100 mg/ml $ZnCl_2$ in an HCl solution having pH 2.7 water. 1 mg of the compound of Example 1 was dissolved in 250 µl of this solution to yield a clear solution having 4 mg/ml of the compound and 0.5 mg/ml Zn at pH 4.

E. Preparation of Peptide/Zinc Suspension/Gel Having pH=7.0

A particle suspension or gel of a test compound at pH 7.0 for use in in vivo pharmacodynamic ("PD") studies may be made using the following procedure.

Approximately 250 µL of the clear solution made in Preparation D., above, (pH 4, 0.5 mg/ml Zn, 4 mg/ml compound of Example 1) is neutralized to pH 7.0 using approximately 25 µL 0.2 N NaOH.

F. Determination of pI Using IEF Gels

Invitrogen's Novex IEF pH3-10 gels were used to measure the pi of GLP-1 peptides.

Peptidyl compounds to be tested were dissolved in water to a concentration of 0.5 mg/ml. For each such compound, 5 ii of the resulting solution was mixed with 5 µl of Novex® Sample Buffer 2X (comprised of 20 mM Arginine free base, 20 mM Lysine free base and 15% Glycerol) and the resulting 10 µl sample solution was loaded onto the gel along with a protein standard sample.

Running buffers were also obtained from Invitrogen and the gel was run according to manufacture's instructions, generally as follows: 100 V constant for 1 hour, followed by 200 V constant for 1 hour, followed by 500 V constant for 30 minutes.

The gel was then fixed in 12% TCA containing 3.5% sulfosalicylic acid for 30 minutes, and then stained for 2 hours with Colloidal Coomassie Blue according to the instructions found on the Novex® Colloidal Blue Kit thereafter, then de-stained in water overnight.

The gel was scanned and analyzed by the program Fragment Analysis 1.2. pI's of unknown peptides were calculated relative to the pI's of standard compounds having pI values of: 10.7, 9.5, 8.3, 8.0, 7.8, 7.4, 6.9, 6.0, 5.3, 5.2, 4.5, 4.2, and 3.5.

Preferred compounds that may be used to practice the invention have pI values of approximately 6.0 to approximately 8.5, more preferred approximately 6.5 to approximately 8.0, even more preferred approximately 7.0 to approximately 7.8. Surprisingly, compositions of the invention which are particularly well adapted for use were found to have pI's approximating physiologic pH.

G. In Vivo Assays

Compositions of the present invention can be and were tested to determine their ability to promote and enhanced effect in vivo using the following assays.

G.1. Experimental Procedure:

The day prior to the experiment, adult male Sprague-Dawley rats (Taconic, Germantown, N.Y.) that weighed approximately 300-350g were implanted with a right atrial jugular cannula under chlorohydrate anesthetic. The rats were then fasted for 18 hours prior to the injection of the appropriate test composition or vehicle control at time 0. The rats continued to be fasted throughout the entire experiment.

At time zero the rats were injected subcutaneously (sc) either with (a) the compound of Example 1 ($Aib^{8,35}, Arg^{26,34}, Phe^{31}$)hGLP-1(7-36)$NH_2$) at pH 4.0 as a clear solution (i.e., the solution of Preparation D.), or (b) the compound of Example 1 at pH 7.0 as a suspension or gel (i.e., the suspension or gel of Preparation E.). In both cases the injection volume was very small (4-6 µL) and the dose of GLP-1 compound administered to the subject was 75 µg/kg. At the appropriate time after the sc injections a 500 µl blood sample was withdrawn via the intravenous (iv) cannula and the rats were given an iv glucose challenge to test for the presence of enhanced insulin secretion. The times of the glucose challenge were 0.25, 1, 6, 12 and 24 hours post-compound injection. After the initial blood sample was withdrawn glucose (1 g/kg) was injected iv and flushed in with 500 µl heparinized saline (10U/mL). Thereafter, 500 µl blood samples were withdrawn at 2.5, 5, 10 and 20 minutes post-glucose injection. Each of these was immediately followed by an iv injection of 500 µl heparinized saline (10U/mL) through the cannula. The blood samples were centrifuged, plasma was collected from each sample and the samples were stored at –20° C. until they were assayed for insulin content. The amount of insulin in each sample was determined using a rat insulin enzyme-linked immunosorbant assay (ELISA) kit (American Laboratory Products Co., Windham, N.H.).

Results:

Surprisingly, with both the clear solution and suspension or gel form of the compound of Example 1 a sustained insulin-enhancing activity was observed that was inducible by glucose injection over the full 24 hours of the experiment.

G.2. Experimental Procedure:

The assay was performed as in G.1., with the exception that at time zero the rats were injected subcutaneously (sc) with a solution of ($Aib^{8,35}$)hGLP1(7-36)$NH_2$ prepared according to Preparation D., above, or with vehicle control. As in G.1. the injection volume was very small (4-6 µL) and the dose of GLP-1 compound administered to the subject was 75 µg/kg.

Results:

A sustained insulin-enhancing activity was observed that was inducible by glucose injection over the full 24 hours of the experiment.

G.3. Experimental Procedure:

The general procedure was the same as that provided in G.1. In this case the compound of Example 1 prepared according to Preparation D, or a vehicle control, was injected subcutaneously ("sc") at time zero. The time points for the glucose challenge were 1, 6, 12, 24, 48 and 72 hours post-injection. The glucose injection via the iv cannula and subsequent blood sampling were performed as in experiment G.1. Because of the extended fasting period, vehicle and glucose-only controls were included at each time point.

Results:

A sustained insulin-enhancing activity that was inducible by glucose for at least 48 hours after subcutaneous injection of the test composition was observed. In addition, as in experiment G.1. no initial high level of insulin enhancement in response to glucose was observed.

H. In Vivo Assays

Compositions of the present invention can be and were tested to determine their ability to promote extended release of active compound in vivo using assays H.1-H.4., described below. As a representative example of compounds that may be used to practice the invention, the compound of Example 1, (Aib$^{8,35}$, Arg$^{26,4}$, Phe$^{31}$)hGLP-1(7-36)NH$_2$, was formulated into the various exemplary formulations described in Table 3, below, and subjected to assays H.1.-H.4.

Compositions for use in the assays below were made according to the following general procedure:

Stock solutions of 100 mg/ml ZnCl$_2$ were made by dissolving zinc chloride (Merck, Mollet del Valles, Barcelona, Spain) in sterile water for injection (Braun, Rubi, Spain) which had been adjusted to pH 2.7 using HCl. Solutions containing zinc at various concentrations, e.g., 0.1 mg/ml, 0.5 mg/ml, 2 mg/ml, etc., were obtained by dilution of the stock solution. Solutions containing zinc at lower concentrations, e.g., 10 µg/ml, 20 µg/ml, 30 µg/ml, were prepared in an analogous manner by dilution of a stock solution comprising 1 mg/ml ZnCl$_2$.

An appropriate amount of a compound to be assayed, e.g., the peptide of Example 1, was weighed and dissolved in the appropriate volume of each resulting zinc solution to yield a clear solution having a desired concentration of the compound; e.g., 4 mg/ml. The resulting solutions were then micro-filtered and, if necessary, stored in light-protected vials before administration.

The concentration of test compound in the plasma of the test subjects may be determined by a number of methods known in the art. In one convenient method the concentration of a compound, e.g., the compound of Example 1, is determined via radioimmunoassay employing a rabbit derived antibody to the test compound in competition with a known quantity of test compound that has been radio-iodinated with, e.g., $^{125}$I.

H.1. Pharmacokinetic Study 1

The effect of zinc on the bioavailability of a bioactive compound administered to a subject using a composition according to the invention can be and was determined as follows.

Following the procedures described above, four aqueous compositions were formulated to have 4 mg/mL of the Compound of Example 1 at pH=2.7, and 0.0, 0.1, 0.5, and 2.0 mg/ml of ZnCl$_2$, respectively. See Table 3, Examples H1a, H1b, H1c and H1d. Each of the four compositions was administered subcutaneously to 16 Sprague-Dawley rats (Charles River Laboratories, Wilmington, Mass., USA). The average age of the rats was approximately 8-9 weeks, and the average weight was approximately 260-430 g. The rats were provided food and water ad libitum. The plasma levels of the compound of Example 1 after injection (dose=75 microg/kg compound of Example 1) are depicted in FIG. 1.

H.2. Pharmacokinetic Study 2

The effect of injection volume on the bioavailability of a bioactive compound administered to a subject using a composition according to the invention can be and was determined as follows.

Figure 2:
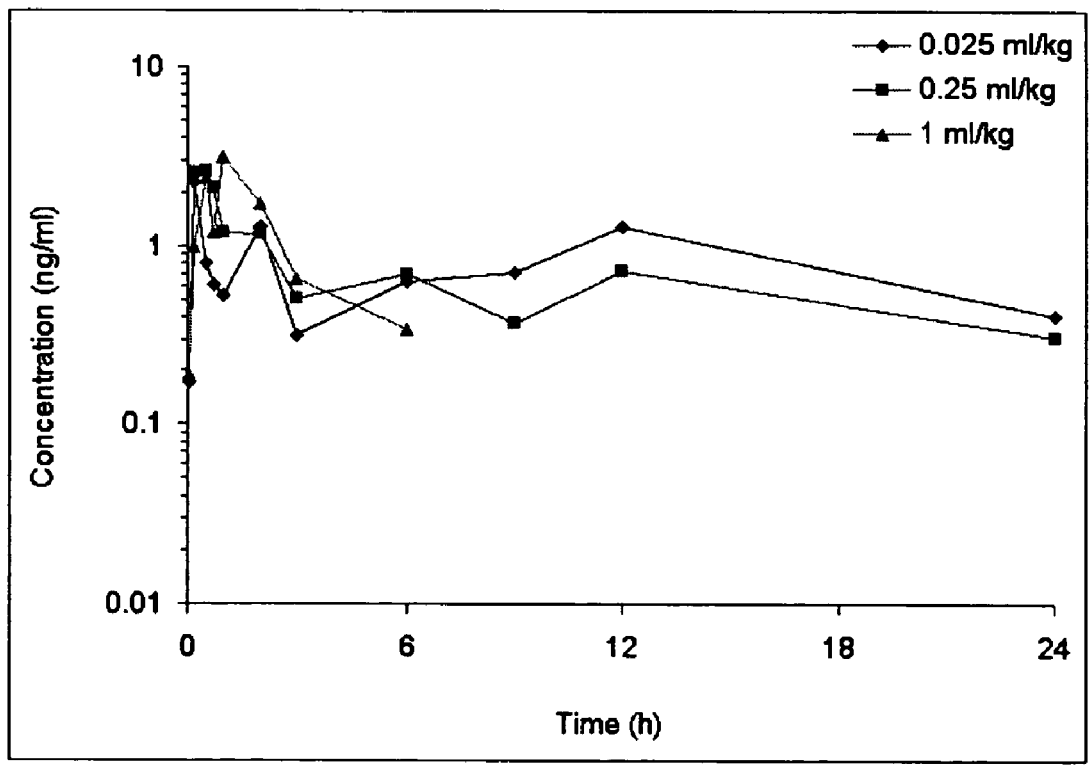
FIG. 2 depicts the time course plasma concentration of a peptide administered to rats using compositions according to the invention, according to Example H.2.

Following the procedures described above, three aqueous compositions were formulated to have 3000, 300 and 75 microg/mL, respectively, of the Compound of Example 1, at a pH of 2.7 and Zn concentration of 0.5 mg/ml. See Table 3, Examples H2a, H2b, and H2c. Each of the three compositions was administered subcutaneously to 16 Sprague-Dawley rats (Charles River Laboratories, Wilmington, Mass., USA). The average age of the rats was approximately 8-10 weeks and the average weight was approximately 330-460 g. The rats were fasted overnight prior to commencement of the study. The volume of injection was selected to provide each rat with 75 microg/kg dose of the compound of Example 1. (0.025 ml/kg, 0.25 ml/kg, and 1 ml/kg, respectively.) The plasma levels of the compound of Example 1 after injection are depicted in FIG. 2.

H.3. Pharmacokinetic Study 3

The effect of zinc on the bioavailability of a bioactive compound administered to a subject using a composition according to the invention can be and was determined as follows.

Figure 3:
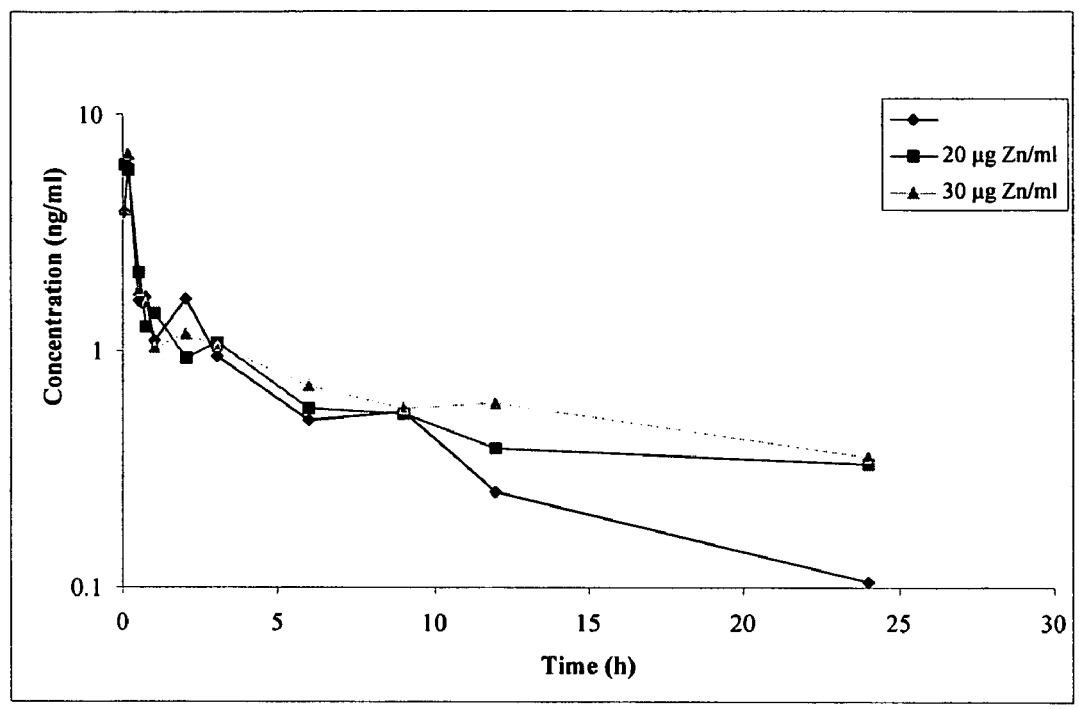
FIG. 3 depicts the time course plasma concentration of a peptide administered to rats using compositions according to the invention, according to Example H.3.

Following the procedures described above, three aqueous compositions were formulated to have 4 mg/mL of the Compound of Example 1 at pH=2.7, and 10, 20 and 30 microg/mL of zinc, respectively. See Table 3, Examples H3a, H3b, and H3c. Each of the three compositions was administered subcutaneously to 16 Male albino Sprague-Dawley rats (St. Feliu de Codines, Barcelona, ES). These rats were fasted overnight prior to commencement of the study. The plasma levels of the compound of Example 1 after injection (dose=75 microg/kg compound of Example 1) are depicted in FIG. 3.

H.4. Pharmacokinetic Study 4

The effect of zinc and bioactive compound concentrations on the bioavailability of the bioactive compound when administered to a subject using a composition according to the invention can be and was determined as follows.

Figure 4:
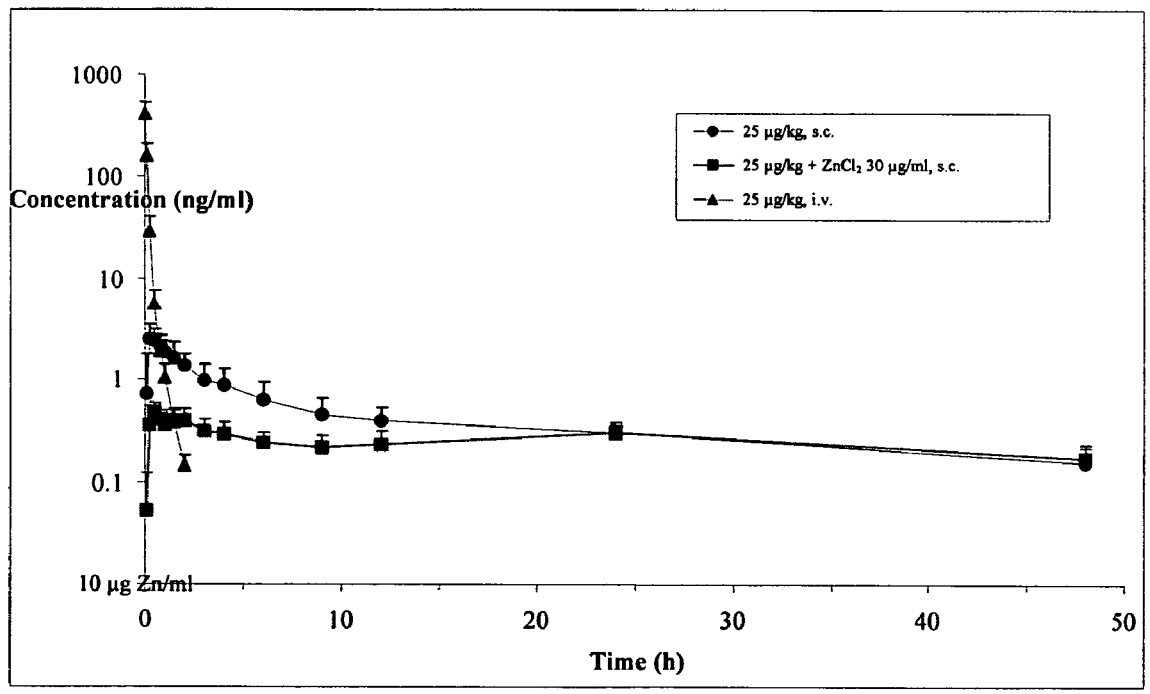
FIG. 4 depicts the time course plasma concentration of a peptide administered to beagle dogs using compositions according to the invention, according to Example H.4.

Following the procedures described above, two aqueous compositions were formulated. The first solution comprised 1.45 mg/ml of the compound of Example 1 and 30 micorg/ml Zinc, the second comprised 1.45 mg/ml of the compound of Example 1 but without zinc. Both solutions had pH=2.7. See Table 3, Example H4a and H4b. Each solution was administered subcutaneously to male Beagle dogs (Isoquimen, Barcelona, Spain) ranging in age from approximately 54-65 months and in weight from approximately 16-21 kg. The dogs were fasted overnight prior to commencement of the study. Additionally, the second solution containing only active compound was administered intravenously. All injections provided doses of 25 microg/kg. The plasma levels of the Compound of Example 1 after injection are depicted in FIG. 4.

TABLE 3

Summary of compositions tested

| Example | Components | Amount | Units |
|---------|------------|--------|-------|
| H1a | Active Compound: Example 1 | 4 | mg |
|  | Solution pH = 2.7 | 1 | mL |
| H1b | Active Compound: Example 1 | 4 | mg |
|  | Solution 0.1 mg/mL ZnCl$_2$ in WFI (pH = 2.7) | 1 | mL |
| H1c | Active Compound: Example 1 | 4 | mg |
|  | Solution 0.5 mg/mL ZnCl$_2$ in WFI (pH = 2.7) | 1 | mL |
| H1d | Active Compound: Example 1 | 4 | mg |
|  | Solution 2 mg/mL ZnCl$_2$ in WFI (pH = 2.7) | 1 | mL |
| H2a | Active Compound: Example 1 | 3 | mg |
|  | Solution 0.5 mg/mL ZnCl$_2$ in WFI | 1 | mL |
| H2b | Active Compound: Example 1 | 300 | µg |
|  | Solution 0.5 mg/mL ZnCl$_2$ in WFI | 1 | mL |

TABLE 3-continued

Summary of compositions tested

| Example | Components | Amount | Units |
|---|---|---|---|
| H2c | Active Compound: Example 1 | 75 | µg |
| | Solution 0.5 mg/mL ZnCl$_2$ in WFI | 1 | mL |
| | Solution NaOH 7 M | 8 | µL |
| H3a | Active Compound: Example 1 | 4 | mg |
| | Solution 10 microg/ml ZnCl$_2$ in WFI | 1 | ml |
| H3b | Active Compound: Example 1 | 4 | mg |
| | Solution 20 microg/ml ZnCl$_2$ in WFI | 1 | ml |
| H3c | Active Compound: Example 1 | 4 | mg |
| | Solution 30 microg/ml ZnCl$_2$ in WFI | 1 | ml |
| H4a | Active Compound: Example 1 | 1.45 | mg |
| | WFI | 1 | Ml |
| H4b | Active Compound: Example 1 | 1.45 | mg/Ml |
| | Solution 30 microg/ml ZnCl$_2$ in WFI | 1 | ml |

WFI = sterile water for injection (BRAUN, Rubi, Spain)

I. In Vivo Assays

I.1. Pharmacokinetic Study: Semi-solid composition

The ability of semi-solid aqueous compositions of the invention to provide a biologically significant plasma concentration of peptide over a further extended period of time after administration to a subject can be and was determined as follows.

Figure 5:
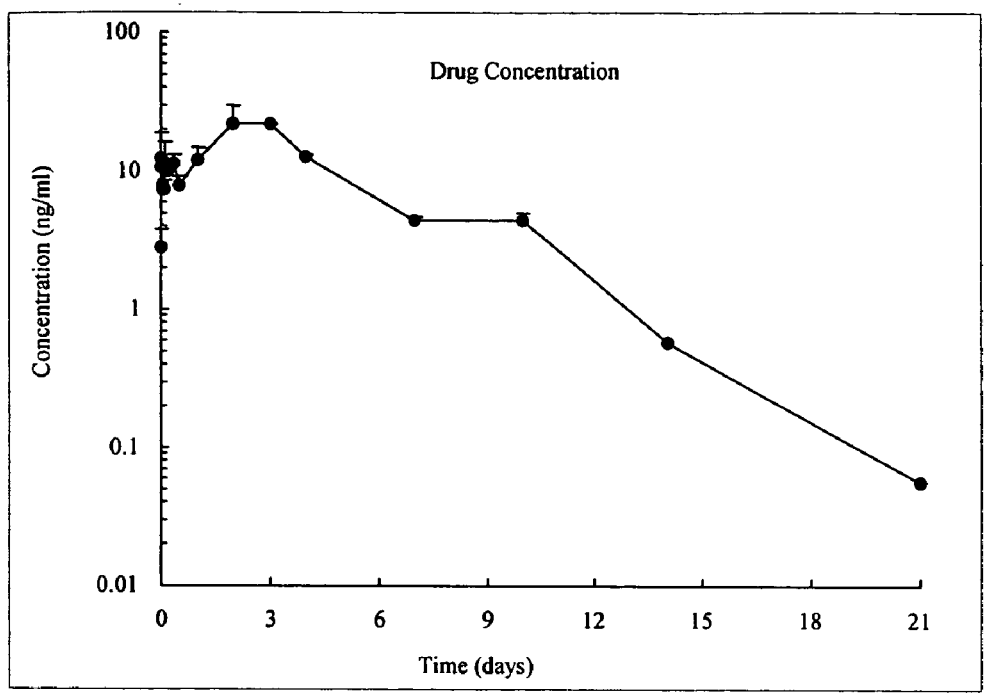
FIG. 5 depicts the time course plasma concentration of a peptide administered to rats using compositions according to the invention, according to Example 1.1.

An aqueous semi-solid composition of the Compound of Example 1 was made by homogenizing an amount of the Compound of Example 1 (acetate salt) with sufficient sterile water for injection to provide a semi-solid, paste-like composition which comprised approximately 25% of the peptide (e.g., 0.250 mg/mg). The composition was loaded into 0.3 mL syringes fitted with 19/0.6 (0.35 mm) UNIMED needles. Approximately 60 mg of the semi-solid composition (containing approximately 15 mg of peptide) was administered to each of 10 male Sprague-Dawley rats (Harlan Iberica, Barcelona, Spain). The average age of the rats was approximately 10 weeks, and the average weight was approximately 220-330 g. The rats were fasted approximately 14 hours prior to commencement of the study, however they were provided with water ad libitum. The rats were provided with food and water ad libitum after administration of the test composition. The plasma levels of the compound of Example 1 after injection are depicted in FIG. 5.

I.2. Pharmacokinetic Study: 1 mg Microtablet

The ability of a solid composition of the invention, without zinc, diluent, or other excipient, also to provide a biologically significant plasma concentration of peptide over a further extended period of time after administration to a subject can be and was determined as follows.

Figure 6:
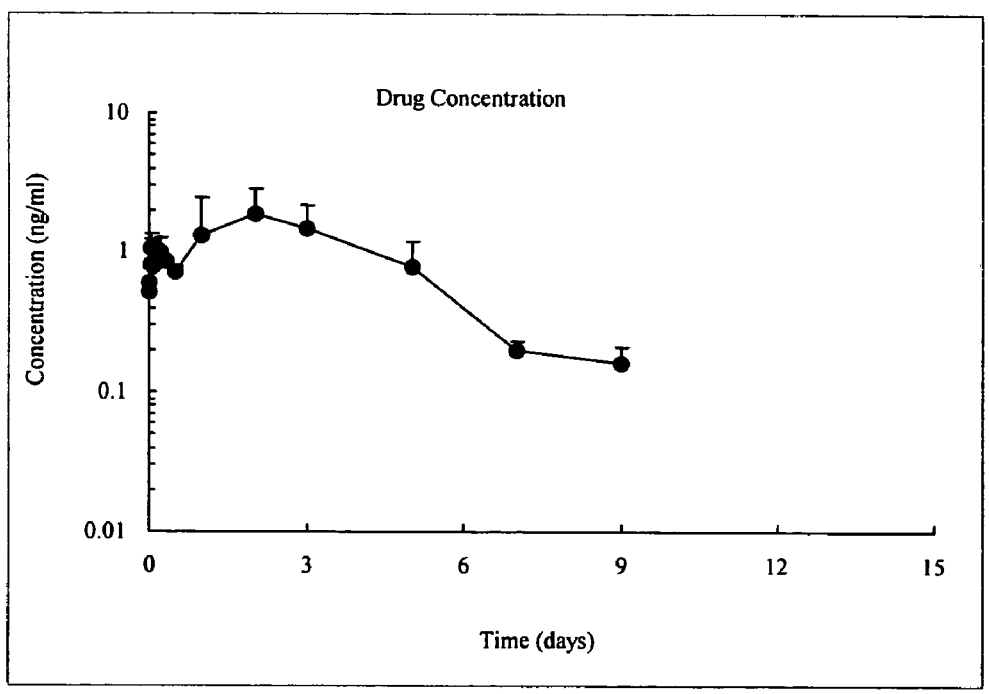
FIG. 6 depicts the time course plasma concentration of a peptide administered to rats using compositions according to the invention, according to Example 1.2.

Samples of such weight of the acetate salt of the Compound of Example 1 as to provide approximately 1 mg of the peptide were added to a standard tableting die and compressed to form solid microtablets. The microtablets were loaded into ICO plunger syringes fitted with a 1.2/1.0 (0.25 mm) needles; i.e., having a 1 mm internal diameter. The mircotablets were administered to each of 10 male Sprague-Dawley rats (Charles River Laboratories). The age of the rats ranged from approximately 10-12 weeks, and the weight ranged from approximately 320-480 g. The rats were fasted approximately 14 hours prior to commencement of the study, however they were provided with water ad libitum. The rats were provided with food and water ad libitum after administration of the test composition. The plasma levels of the compound of Example 1 after injection are depicted in FIG. 6.

I.pb 3. Pharmacokinetic Study: 15 mg Microtablet

Figure 7:
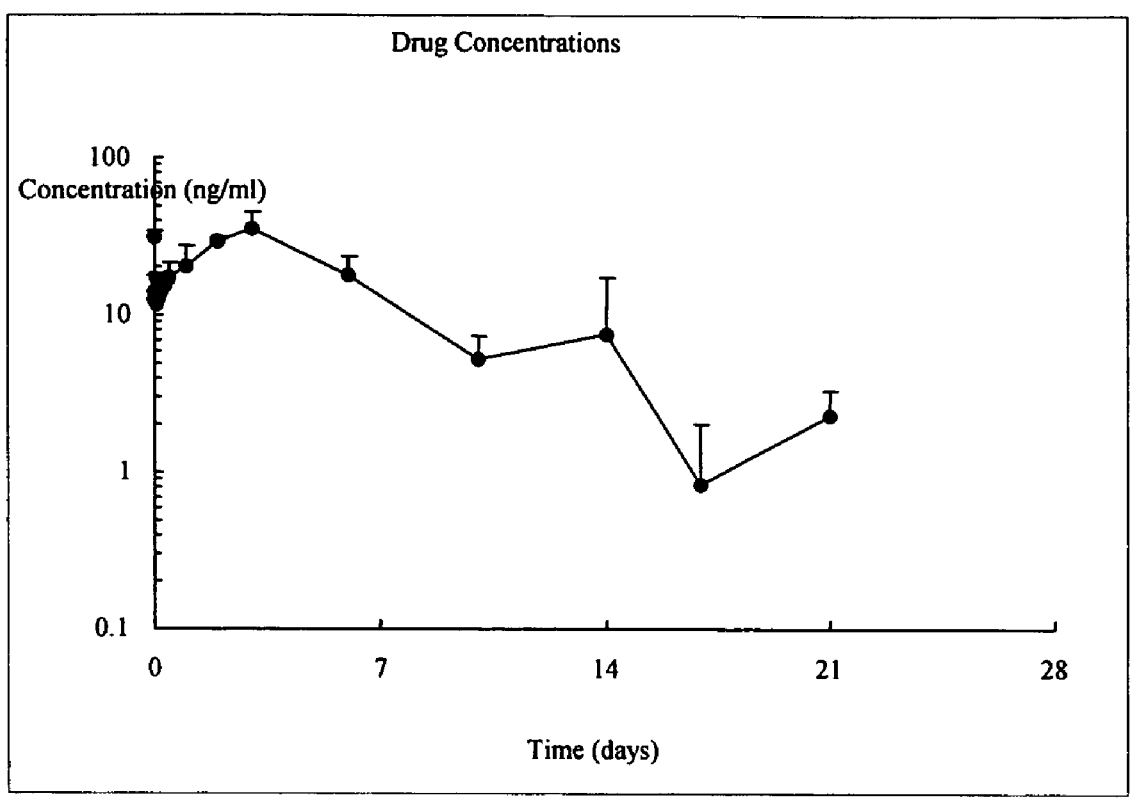
FIG. 7 depicts the time course plasma concentration of a peptide administered to rats using compositions according to the invention, according to Example 1.3.

Substantially the same procedure was employed as provided for study 1.3., above, with the exception that the microtablets were formulated to contain 15 mg of the Compound of Example 1. The age of the rats ranged from approximately 11-13 weeks, and the weight ranged from approximately 300-480 g. The plasma levels of the compound of Example 1 after injection are depicted in FIG. 7.

In the figures depicting the results of the foregoing in vivo examples the points plotted represent the mean values of the tested populations.

The peptides used in this invention advantageously may be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution for 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of GLP-1 is varied and multitudinous (See, Todd, J. F., et al., Clinical Science, 1998, 95, pp. 325-329; and Todd, J. F. et al., European Journal of Clinical Investigation, 1997, 27, pp.533-536). Thus, the administration of the compounds of this invention for purposes of eliciting an agonist effect can have the same effects and uses as GLP-1 itself. These varied uses of GLP-1 may be summarized as follows, treatment of: Type I diabetes, Type II diabetes, obesity, glucagonomas, secretory disorders of the airway, metabolic disorder, arthritis, osteoporosis, central nervous system diseases, restenosis, neurodegenerative diseases, renal failure, congestive heart failure, nephrotic syndrome, cirrhosis, pulmonary edema, hypertension, and disorders wherein the reduction of food intake is desired. GLP-1 analogues of the present invention that elicit an antagonist effect from a subject can be used for treating the following: hypoglycemia and malabsorption syndrome associated with gastroectomy or small bowel resection.

Accordingly, the present invention includes within its scope pharmaceutical compositions as defined herein comprising, as an active ingredient, at least one of the compounds of formula (I).

The dosage of active ingredient in the formulations of this invention may be varied; however, it is necessary that the amount of the active ingredient be such that a suitable dosage is obtained. The selected dosage depends upon the desired therapeutic effect, on the route of administration, and on the duration of the treatment, and normally will be determined by the attending physician. In general, an effective dosage for the activities of this invention is in the range of $1\times10^{-7}$ to 200 mg/kg/day, preferably $1\times10^{-4}$ to 100 mg/kg/day, which can be administered as a single dose or divided into multiple doses.

The formulations of this invention are preferably administered parenterally, e.g., intramuscularly, intraperitoneally, intravenously, subcutaneously, and the like.

Preparations according to this invention for parenteral administration include sterile aqueous or non-aqueous solutions, suspensions, gels, or emulsions, provided that the desired in vivo release profile is achieved. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

What is claimed is:

1. A pharmaceutical composition comprising an analog according to the formula:

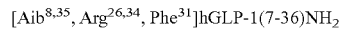

$[Aib^{8,35}, Arg^{26,34}, Phe^{31}]hGLP-1(7-36)NH_2$ together with zinc and a pharmaceutically acceptable carrier or diluent.

2. A composition according to claim 1, wherein said zinc is present in a concentration from 0.0005 mg/mL to 50 mg/mL.

3. A pharmaceutical composition according to claim 1 or 2 wherein said composition forms a precipitate after subcutaneous administration to a subject.

4. A composition according to claims 1 or 2, wherein the analog is present in an aqueous solution with a pH lower than 7.

5. A composition according to claims 1 or 2, wherein the analog is present in a concentration of about 0.001-500 mg/mL.

6. A composition according to claim 2, wherein said zinc is present in a concentration from 0.01 mg/mL to 0.50 mg/mL.

7. A composition according to claim 4, wherein the analog is present in an aqueous solution with a pH lower than 5.

8. A composition according to claim 5, wherein the analog is present in a concentration of about 0.1-10 mg/mL.

9. A composition according to any one of claims 1, 2, 6, 7, and 8, wherein said diluent comprises a pharmaceutically acceptable aqueous solution.

* * * * *